US012708561B2

(12) United States Patent
Shoham-Hazon et al.

(10) Patent No.: US 12,708,561 B2
(45) Date of Patent: Aug. 18, 2026

(54) MEDICAL DEVICE FOR DEPLOYMENT WITHIN AN EYE FOR MANAGEMENT OF INTRAOCULAR FLUIDS

(71) Applicant: Hexiris Inc., Dieppe (CA)

(72) Inventors: Nir Shoham-Hazon, Miramichi (CA); Houfar Sekhavat, Dieppe (CA); Kenneth Dale Johannaber, Reno, NV (US)

(73) Assignee: Hexiris Inc., Dieppe (CA)

( * ) Notice: Subject to any disclaimer, the term of this patent is extended or adjusted under 35 U.S.C. 154(b) by 0 days.

(21) Appl. No.: 19/393,301

(22) Filed: Nov. 18, 2025

(65) Prior Publication Data

US 2026/0124072 A1 May 7, 2026

Related U.S. Application Data

(63) Continuation of application No. PCT/CA2025/051476, filed on Nov. 6, 2025.

(Continued)

(30) Foreign Application Priority Data

Nov. 19, 2024 (GB) ..................................... 2416974

(51) Int. Cl.
*A61F 9/007* (2006.01)

(52) U.S. Cl.
CPC .. *A61F 9/00781* (2013.01); *A61F 2210/0014* (2013.01); *A61F 2250/0039* (2013.01)

(58) Field of Classification Search
CPC .......... A61F 9/00781; A61F 2210/0014; A61F 2250/0039
See application file for complete search history.

(56) References Cited

U.S. PATENT DOCUMENTS 5,092,837 A * 3/1992 Ritch .................. A61F 9/00781 604/294
6,471,666 B1 * 10/2002 Odrich ................ A61F 9/00781 606/108

(Continued)

FOREIGN PATENT DOCUMENTS

EP 2954873 B1 11/2019

OTHER PUBLICATIONS

Combined Search and Examination Report for UK Application No. GB2416974.0, dated Apr. 3, 2025.

*Primary Examiner* — Leslie R Deak
(74) *Attorney, Agent, or Firm* — MARSHALL, GERSTEIN & BORUN LLP

(57) ABSTRACT

The disclosure relates to ophthalmic implants, specifically a flexible, self-expanding spacer device deployable in subconjunctival, sub-Tenon's, or suprachoroidal spaces to manage intraocular fluids. The device addresses limitations of fixed-resistance drainage and fibrosis-related failure in glaucoma surgery by maintaining a controlled three-dimensional reservoir (bleb space) for aqueous humor outflow while minimizing tissue trauma. In one aspect, a shape-memory body transitions from a compressed, delivery-compatible state to an expanded configuration defining a convex internal volume, optionally with collapse-resistant reinforcements and tissue-engaging elements for atraumatic stabilization. Preferred embodiments include anterior relief geometry to avoid corneal contact and posterior flow-directing features to promote posterior bleb formation and uniform pressure control. A delivery member with a reduced-profile, tapered piercing tip and optional bent shaft enables minimally invasive ab externo implantation and controlled, coaxial deployment. Advantages include streamlined single-step delivery, stable long-term bleb architecture, reduced (Continued)

hypotony and fibrotic encapsulation, and compatibility with trabeculectomy and shunt-based outflow.

15 Claims, 32 Drawing Sheets

Related U.S. Application Data

(60) Provisional application No. 63/828,578, filed on Jun. 23, 2025, provisional application No. 63/716,920, filed on Nov. 6, 2024.

(56) References Cited

U.S. PATENT DOCUMENTS

| | | | | |
|---|---|---|---|---|
| 6,881,197 | B1 * | 4/2005 | Nigam ................ | A61M 27/006 604/9 |
| 8,353,856 | B2 * | 1/2013 | Baerveldt ........... | A61F 9/00781 604/9 |
| 8,529,492 | B2 * | 9/2013 | Clauson .................. | A61P 27/02 604/93.01 |
| 9,039,650 | B2 | 5/2015 | Schieber et al. | |
| 2007/0265582 | A1 * | 11/2007 | Kaplan ............. | A61M 37/0069 604/260 |
| 2019/0038463 | A1 | 2/2019 | Kasic | |
| 2021/0030590 | A1 * | 2/2021 | Blanda .................. | A61F 9/0026 |

* cited by examiner

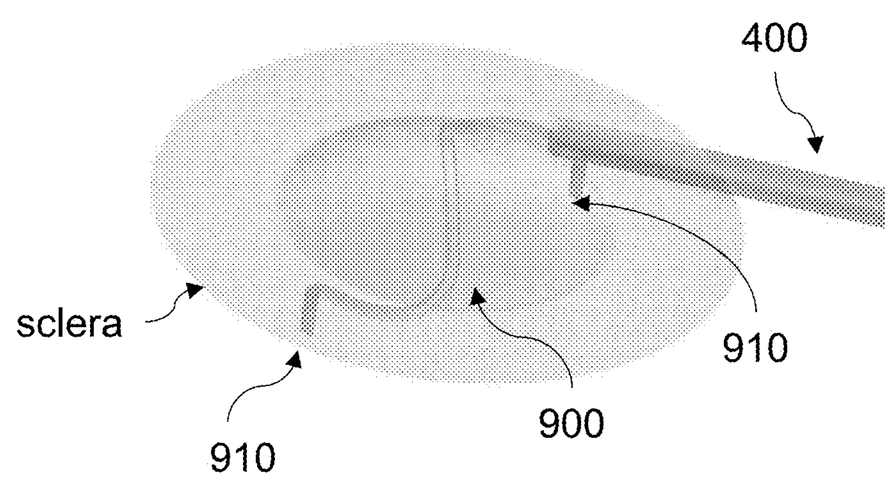
FIG. 9H
FIG. 9I
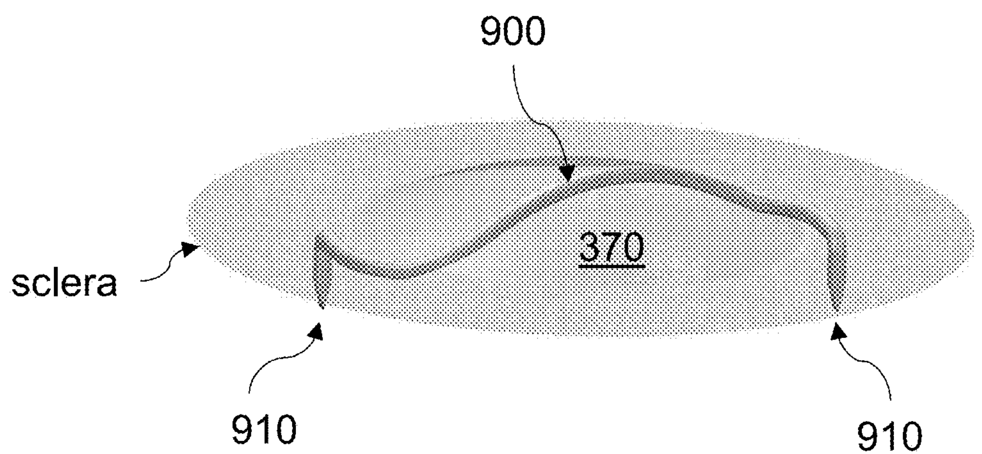

FIG. 11C – Prior art

FIG. 12A
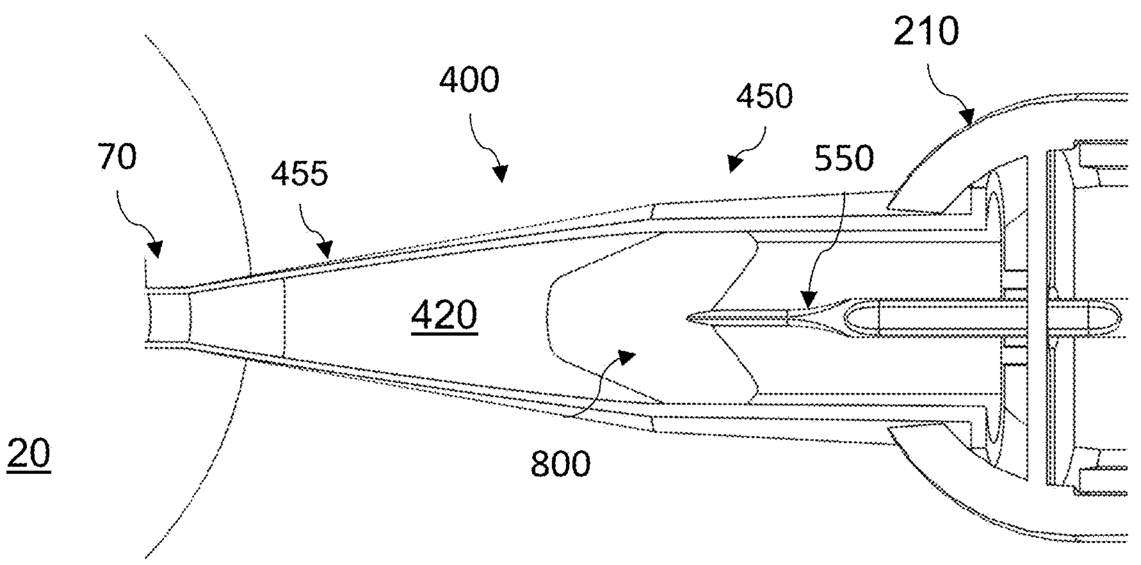
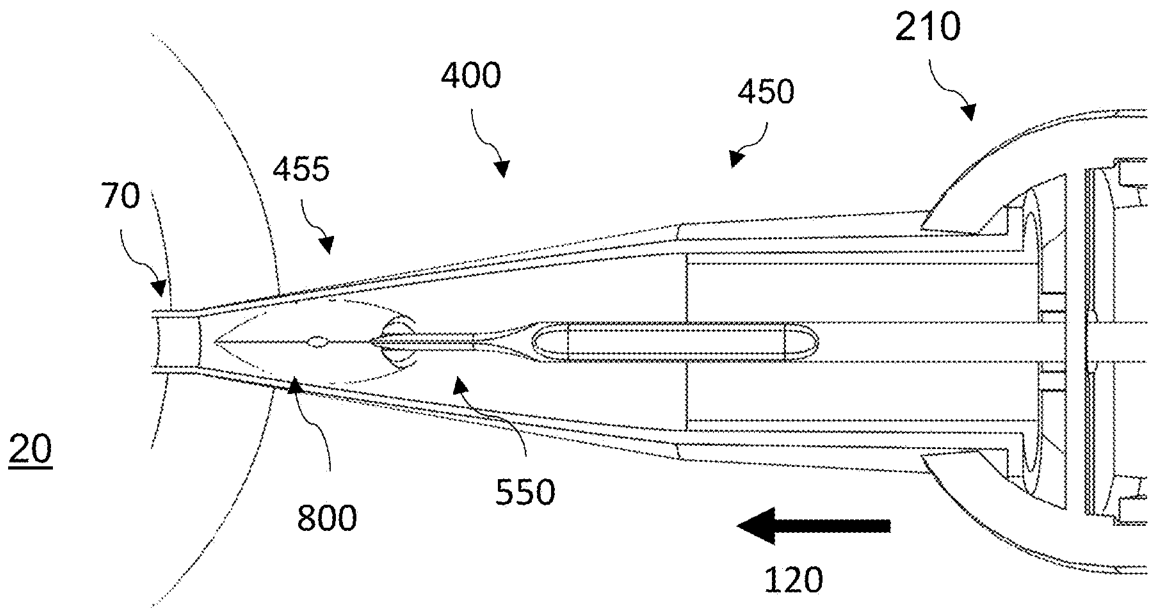
FIG. 12B

550

560
880
800
820
880
845
820
870
550
800
845

820
870

800
f
f
f 20
800
f
f
f

800 f
f 20
800
f
f

FIG. 16A
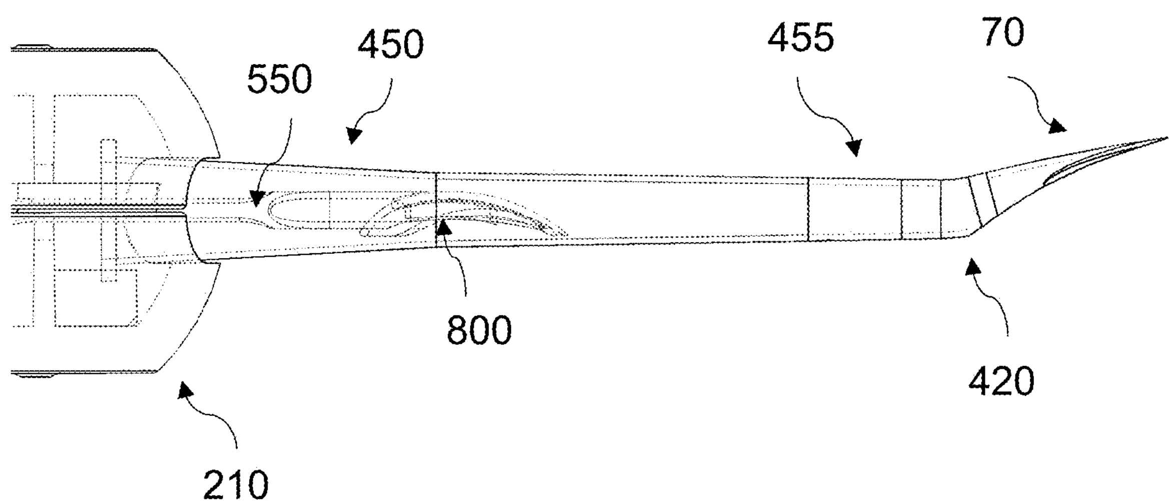
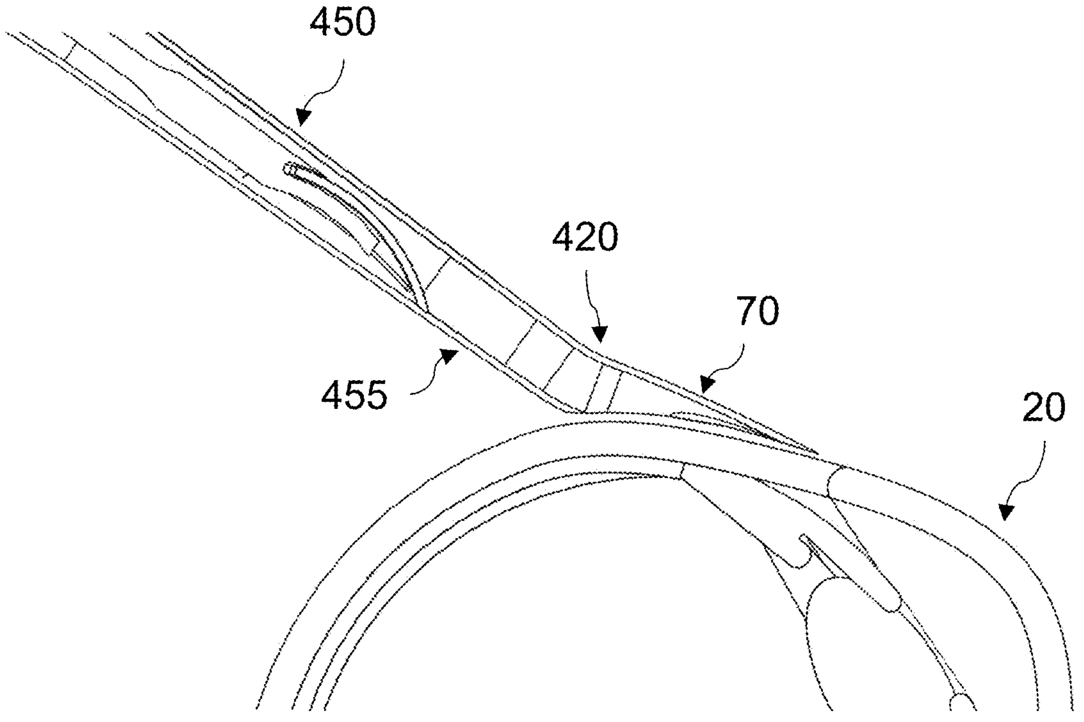
FIG. 16B

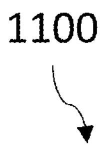

positioning a delivery member housing a spacer device in a contracted configuration, at a first point with respect to the eye
1110 advancing along the longitudinal axis until the delivery member contacts the external surface of a tissue layer
1120

Performing an incision in the eye tissue layer with the delivery member distal end
1130 causing delivery of the spacer device in the eye, the delivery device deploying into an expanded configuration and forming a three-dimensional volume
1140

FIG. 17

MEDICAL DEVICE FOR DEPLOYMENT WITHIN AN EYE FOR MANAGEMENT OF INTRAOCULAR FLUIDS

CROSS-REFERENCE TO RELATED APPLICATIONS

The present application is a continuation patent application based on International patent application number PCT/CA2025/051476 filed on Nov. 6, 2025, which claims the benefit of U.S. provisional patent application Ser. No. 63/716,920 filed on Nov. 6, 2024, British patent application serial number 2416974.0 filed on Nov. 19, 2024, and U.S. provisional patent application Ser. No. 63/828,578 filed on Jun. 23, 2025. The contents of each of the above-referenced documents are incorporated herein by reference in their entirety.

TECHNICAL FIELD

This application generally relates to the field of a spacer device for ophthalmic procedures and, more specifically, to a spacer device for deployment within an eye to create a three-dimensional volume for the management of intraocular fluids.

COPYRIGHT

A portion of the disclosure of this patent document contains material that is subject to copyright protection. The copyright owner has no objection to the facsimile reproduction by anyone of the patent document or the patent disclosure as it appears in the Patent and Trademark Office patent file or records, but otherwise reserves all copyright rights whatsoever.

BACKGROUND

Glaucoma comprises a group of eye disorders characterized by progressive damage to the optic nerve. Elevated intraocular pressure (IOP) is a primary risk factor, and if unmanaged, glaucoma can lead to irreversible vision loss and blindness. Treatments to lower IOP include topical medications, laser procedures, and incisional surgeries; however, a subset of patients does not achieve adequate control with these approaches and may require more advanced surgical interventions.

Glaucoma drainage devices (tube shunts) are used when medical therapy and/or laser procedures are insufficient. Typically fabricated from biocompatible materials such as silicone or polypropylene, these devices provide an alternate outflow pathway for aqueous humor to lower IOP and mitigate further optic nerve damage. Tube shunts are particularly important in refractory glaucoma.

Commonly used devices include, for example, the Ahmed Glaucoma Valve, the Baerveldt Glaucoma Implant, and the Molteno Implant. While differing in size, configuration, and materials, these devices share the objective of facilitating aqueous humor drainage to reduce IOP. By way of example, some devices employ a silicone tube coupled to a plate positioned beneath the conjunctiva or on the scleral surface, with the tube inserted into the anterior chamber.

A significant postoperative challenge is peri-implant scarring (fibrosis), which can impede aqueous outflow and diminish long-term shunt performance. To reduce fibrotic response, anti-fibrotic agents such as mitomycin-C (MMC) and 5-fluorouracil (5-FU) are sometimes used intraoperatively or perioperatively to help maintain device patency.

Despite their utility, anti-fibrotic agents have been associated with potential adverse effects, including corneal toxicity and collateral damage to ocular tissues, leading to ongoing scrutiny of their risk-benefit profiles in glaucoma surgery.

Known tube shunt designs typically provide drainage governed by IOP and a fixed hydrodynamic resistance. Fixed-resistance outflow can be suboptimal across postoperative phases. Shortly after implantation, insufficient resistance may precipitate hypotony (e.g., IOP<6 mmHg), which is associated with complications such as hypotony maculopathy and choroidal detachment. Conversely, over time, progressive fibrosis around the device and distal outflow pathways can increase effective resistance, elevating IOP to non-physiologic levels and compromising long-term pressure control. These limitations highlight a need for improved approaches to regulate aqueous outflow and mitigate both early hypotony and late fibrotic failure.

In view of the above, there remains a need for alternate devices and procedures for ocular surgeries for treatment of ophthalmic conditions, such as glaucoma.

SUMMARY

This Summary is provided to introduce a selection of concepts in a simplified form that are further described below in the Detailed Description. This Summary is not intended to identify key aspects or essential aspects of the claimed subject matter.

As embodied and broadly described herein, the present disclosure relates to a spacer device for implantation in an eye, comprising a flexible body configured to conform to anatomical tissue surfaces of the eye, wherein the spacer device is configured to reversibly transition between a compressed configuration suitable for delivery through a delivery member and an expanded configuration defining a convex, internal three-dimensional volume for receiving fluid from an anterior chamber of the eye, and wherein the spacer device includes one or more engaging elements configured to interface with the delivery member to stabilize the spacer device during implantation in the eye.

As embodied and broadly described herein, the present disclosure also relates to a spacer device for deployment within an eye, comprising: a support structure; at least one deformable member arranged relative to the support structure to define a three-dimensional volume, wherein the support structure and the at least one deformable member are movable between a compressed configuration sized for passage through a lumen of a delivery member and an expanded configuration, wherein in the expanded configuration, the at least one deformable member extends away from the support structure to form a curved shape that defines and contains the three-dimensional volume, and wherein the three-dimensional volume is configured to receive a fluid when the device is deployed within the eye.

As embodied and broadly described herein, the present disclosure also relates to a method of deploying a spacer device within an eye, comprising: providing the spacer device as described herein; inserting a delivery member in the eye, wherein the delivery member houses the spacer device; and delivering the spacer device in the eye, wherein the spacer device self-expands upon deployment from the delivery member.

As embodied and broadly described herein, the present disclosure also relates to a delivery device, comprising a) a body having a proximal and a distal end, b) a spacer device for implantation in an eye, comprising a flexible body configured to conform to anatomical tissue surfaces of the eye, and c) a delivery member having a proximal portion and a distal portion, wherein the proximal portion couples with the distal end of the body, wherein the distal portion has a distal piercing tip, wherein the delivery member defines an internal lumen extending from the distal portion to the proximal portion, and wherein the delivery member contains the spacer device within the lumen, wherein the spacer device is configured to reversibly transition between a compressed configuration suitable for delivery through the delivery member and an expanded configuration defining a convex, internal three-dimensional volume for receiving fluid from an anterior chamber of the eye, wherein the delivery device is configured to cause axial displacement movement of the spacer device through the delivery member in the compressed configuration, and wherein the delivery device is configured to push the spacer device out of the distal tip, causing the spacer device to transition to the expanded configuration.

As embodied and broadly described herein, the present disclosure also relates to a method comprising: a) providing a delivery device comprising i) a body having a proximal and a distal end, ii) a spacer device for implantation in an eye, comprising a flexible body configured to conform to anatomical tissue surfaces of the eye, wherein the spacer device is configured to reversibly transition between a compressed configuration suitable for delivery through a delivery member and an expanded configuration defining a convex, internal three-dimensional volume for receiving fluid from an anterior chamber of the eye, and iii) a delivery member having a proximal portion and a distal portion, wherein the proximal portion couples with the distal end of the body, wherein the distal portion has a distal piercing tip, wherein the delivery member defines an internal lumen extending from the distal portion to the proximal portion, and wherein the delivery member contains the spacer device within the lumen; b) inserting the delivery member into a subconjunctival, sub-Tenon's, or suprachoroidal space of the eye; c) causing axial displacement movement of the spacer device through the delivery member, wherein the spacer device is in the compressed configuration; and d) deploying the spacer device out of the distal tip, wherein the spacer device transitions to the expanded configuration.

As embodied and broadly described herein, the present disclosure also relates to a use of a spacer device comprising a flexible body configured to reversibly transition between a compressed configuration and an expanded configuration defining a convex, internal volume for receiving aqueous humor, for implantation into an eye for the purpose of directing aqueous humor outflow and promoting bleb formation.

As embodied and broadly described herein, the present disclosure also relates to a delivery device, comprising a body having a proximal and a distal end, a spacer device for ocular implantation, comprising a flexible body configured to conform to anatomical tissue surfaces of an eye, a delivery member having a proximal portion which couples with the distal end of the body and having a distal piercing tip, wherein the delivery member defines an internal cavity extending from a distal end to a proximal end thereof, and wherein the delivery member contains the spacer device in the expanded configuration within the lumen, and wherein the piercing tip has a tapered, crescent-shaped or scoop-like structure that gradually narrows an external profile thereof.

All features of exemplary embodiments which are described in this disclosure and are not mutually exclusive can be combined with one another. Elements of one embodiment can be utilized in the other embodiments without further mention. Other aspects and features of the present invention will become apparent to those ordinarily skilled in the art upon review of the following description of specific embodiments in conjunction with the accompanying Figures.

BRIEF DESCRIPTION OF THE DRAWINGS

For a better understanding of the various embodiments described herein, and to show more clearly how these various embodiments may be carried into effect, reference will be made, by way of example, to the accompanying drawings which show at least one example embodiment, and which are now described. The drawings are not intended to limit the scope of the teachings described herein. In the drawings:

FIG. 9F to FIG. 9H are non-limiting illustrations of the implantation procedure for a variant of the spacer device of FIG. 8A, in accordance with non-limiting embodiments of the present disclosure. FIG. 9F shows pressing a first engaging element into the eye sclera. FIG. 9G shows sweeping with the delivery member to deploy the spacer device into an S shape. FIG. 9H shows pressing the second engaging element into the eye sclera.

FIG. 9I is a non-limiting perspective side view of the spacer device of FIG. 9F to FIG. 9H once implanted into the eye sclera, in accordance with non-limiting embodiments of the present disclosure.

FIG. 9J is a non-limiting illustration of the sweeping movement that causes deployment of the spacer device as per the implantation procedure illustrated in FIG. 9F to FIG. 9H, in accordance with non-limiting embodiments of the present disclosure.

FIG. 9K is an elevated view of a variant single wire spacer device of the device of FIG. 7A forming a dome-shape, in accordance with non-limiting embodiments of the present disclosure.

FIG. 11C is a prior art view of a delivery member.

FIG. 12A to FIG. 12C are non-limiting top elevated views of the delivery device of FIG. 11A with a spacer device as described herein, in accordance with non-limiting embodiments of the present disclosure.

FIG. 16A and FIG. 16B are non-limiting cross-sectional diagrams of a delivery member housing the spacer device, where the delivery member includes a bend proximal to the distal end, in accordance with non-limiting embodiments of the present disclosure.

FIG. 17 is a non-limiting flowchart of a method of delivering the spacer device of the present disclosure into an eye, in accordance with non-limiting embodiments of the present disclosure.

Figure 1:
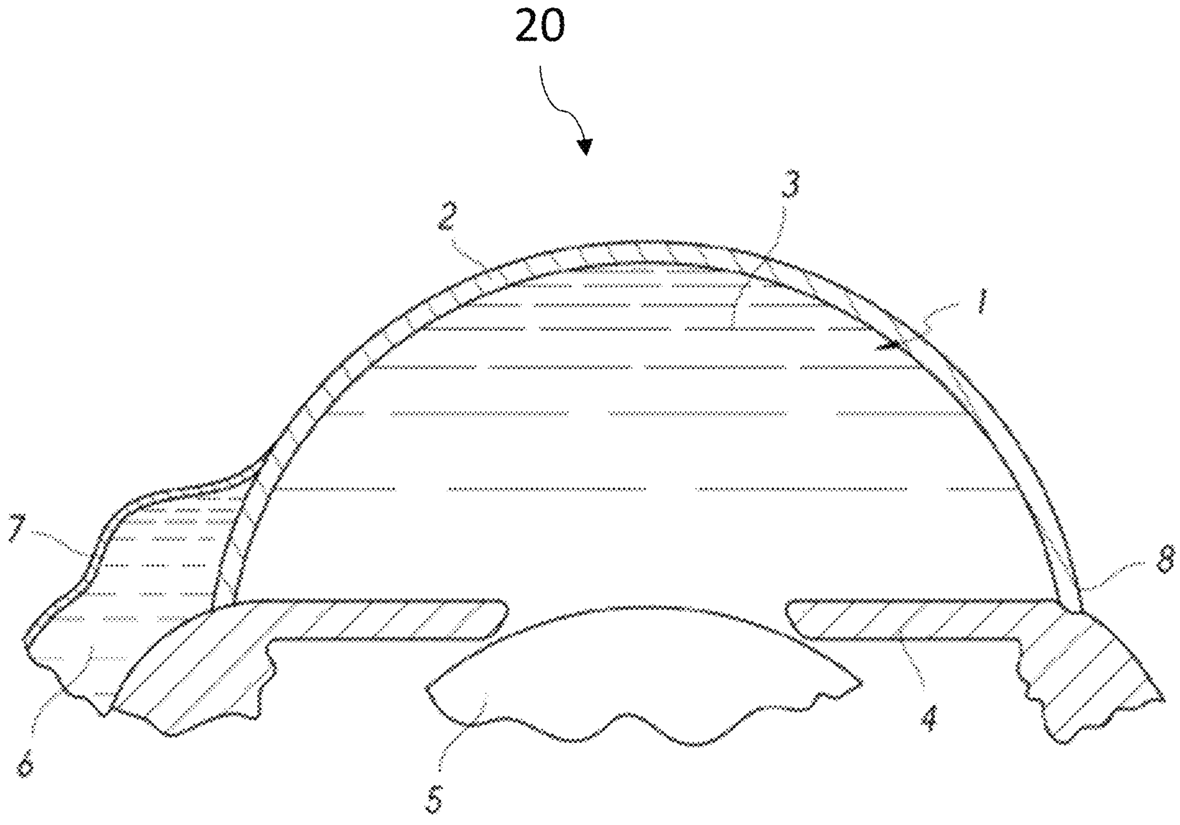
FIG. 1 is a cross-sectional diagram of the general anatomy of a human eye.

In the drawings, exemplary embodiments are illustrated by way of example. It is to be expressly understood that the description and drawings are only for the purpose of illustrating certain embodiments and are an aid for understanding. They are not intended to be a definition of the limits of the invention.

DETAILED DESCRIPTION

The present technology is explained in greater detail below. This description is not intended to be a detailed catalog of all the different ways in which the technology may be implemented, or all the features that may be added to the instant technology. For example, features illustrated with respect to one embodiment may be incorporated into other embodiments, and features illustrated with respect to a particular embodiment may be deleted from that embodiment. In addition, numerous variations and additions to the various embodiments suggested herein will be apparent to those skilled in the art considering the instant disclosure which variations and additions do not depart from the present technology. Hence, the following description is intended to illustrate some embodiments of the technology, and not to exhaustively specify all permutations, combinations, and variations thereof.

In this detailed description and the following claims, specific directional terms are used according to their standard anatomical meanings to describe parts of an eye, implant, or surgical instrument in relation to their orientation or relative positions. For example, "proximal" refers to the portion of an instrument or component that is positioned closest to the torso, while "distal" indicates the part furthest from the torso. Similarly, directional terms such as "anterior" refer to the direction toward the front side of the body, whereas "posterior" designates the direction toward the back side of the body. "Superior" refers to a position above another object or structure, while "inferior" indicates a position below.

Throughout this description, the terms "implant" and "device" may be used interchangeably and refer to the same component or apparatus. These standardized definitions are intended to provide clarity and consistency when describing the invention's components, ensuring precise spatial orientation and anatomical reference within the context of the invention.

The present inventors have developed a spacer device for deployment in the eye. For example, for subconjunctival, sub-Tenon's or suprachoroidal space implantation.

When deployed in the eye, the spacer device exhibits one or more technical advantages that enhance its functionality and effectiveness in ocular applications, such as bleb-forming applications.

For example, the spacer device can have a shape-memory construction, which allows for a straightforward, single-step implantation process. The open, three-dimensional volume which is defined and contained within the spacer device also allows for greater fluid capacity and more efficient management compared to flat or single-channel drainage devices.

For example, the spacer device can have an open structure, which allows it to be folded or compressed for insertion through small incisions, minimizing trauma to ocular tissues. Upon insertion, the spacer device can gently expand to occupy a predefined internal volume, reducing the risk of excessive pressure on surrounding eye structures. This feature is especially valuable in delicate eye surgeries, where reducing the physical footprint of surgical tools is critical to preserving ocular integrity.

Additionally, or alternatively, the open structure can enable unhindered movement of ocular fluids, preventing blockages or disruptions in the natural flow within the eye. This is crucial for maintaining intraocular pressure and avoiding complications like edema or localized tissue compression. Unlike solid implants, which may obstruct fluid pathways, this device's design allows for better integration within the eye's natural physiology, reducing the risk of fluid-related complications. Additionally, the device structure configuration minimizes friction and shear forces on surrounding tissues, enhancing biocompatibility and reducing irritation or inflammation.

For example, the spacer device can have tissue interface structures that include one or more engaging elements that can assist in securing the spacer device within the eye. These engaging elements can be designed to engage with ocular tissue gently but securely, allowing for stable fixation without the need for suture points or adhesives. Alternatively, suture points may also be used. This stability can be advantageous in maintaining precise positioning within the eye, which is particularly important for applications like glaucoma stents or intraocular scaffolds where device displacement could compromise function. The anchoring points also provide an option for fine-tuned adjustments by users (e.g., eye surgeons), who can slightly reposition the spacer device as needed to optimize alignment within the eye's anatomical features.

For example, the spacer device can have an overall curved shape and configuration, which allows the spacer device to conform naturally to the spherical shape of the eye, maximizing its stability and minimizing the potential for irritation. The curved design provides a level of flexibility that accommodates the eye rounded anatomy, helping the device maintain contact over a broader surface area without creating pressure points. This flexibility is especially beneficial in long-term applications, where the device needs to remain in place over extended periods without shifting or causing discomfort.

For example, the spacer device can have one or more collapse-resistant reinforcement features configured to maintain the convex, internal three-dimensional volume in the expanded configuration while permitting elastic compression for delivery, the reinforcement features being integrally formed with or attached to the flexible body. For example, the one or more collapse-resistant reinforcement features may include elongate or contoured stiffening structures that provide anti-collapse support under tissue load, without relying on bulk material thickness. Advantageously, in the expanded state, the one or more collapse-resistant reinforcement features allow the device to maintain a controlled bleb architecture with a low-profile apex height (e.g., about 600-1000 μm) and stable spacing that reduces focal pressure points on ocular tissues.

For example, the spacer device can have a continuous surface defining the three-dimensional volume. In other words, the spacer device can omit perforations through the spacer surface. Such feature can advantageously reduce potential niduses for fibrovascular ingrowth and scarring while preserving an open internal volume and directed flow paths; by contrast, perforations in plate-type designs can act as tissue ingrowth sites that compromise long-term outflow.

For example, the open, internal volume and optional relief and flow-directing geometries can further reduce the likelihood of flow obstruction, fibrosis-related encapsulation, and anterior corneal interactions, thereby improving outflow uniformity and long-term IOP control.

Collectively, these features provide an unexpectedly effective balance of deliverability, atraumatic implantation, and reliable maintenance of a functional bleb space with a reduced profile, addressing the technical problem of achieving minimally invasive implantation while maintaining long-term drainage performance and device stability.

Eye Structure

In accordance with FIG. 1, the general anatomy of an eye 20, such as a human eye, includes the anterior chamber 1, which is bounded by the cornea 2 on its anterior side and the iris 4 on its posterior side. Located beneath the iris 4 is the lens 5, responsible for focusing light onto the retina. The anterior chamber 1 is filled with aqueous humor 3, a fluid that plays a key role in maintaining intraocular pressure. The aqueous humor 3 drains from the anterior chamber through a trabecular meshwork in the sclera 8, which is not depicted in detail in the figure. From there, the fluid exits into a space 6 situated beneath the conjunctiva 7, where it continues to drain into the venous system, ultimately helping to regulate intraocular pressure.

Figure 2:
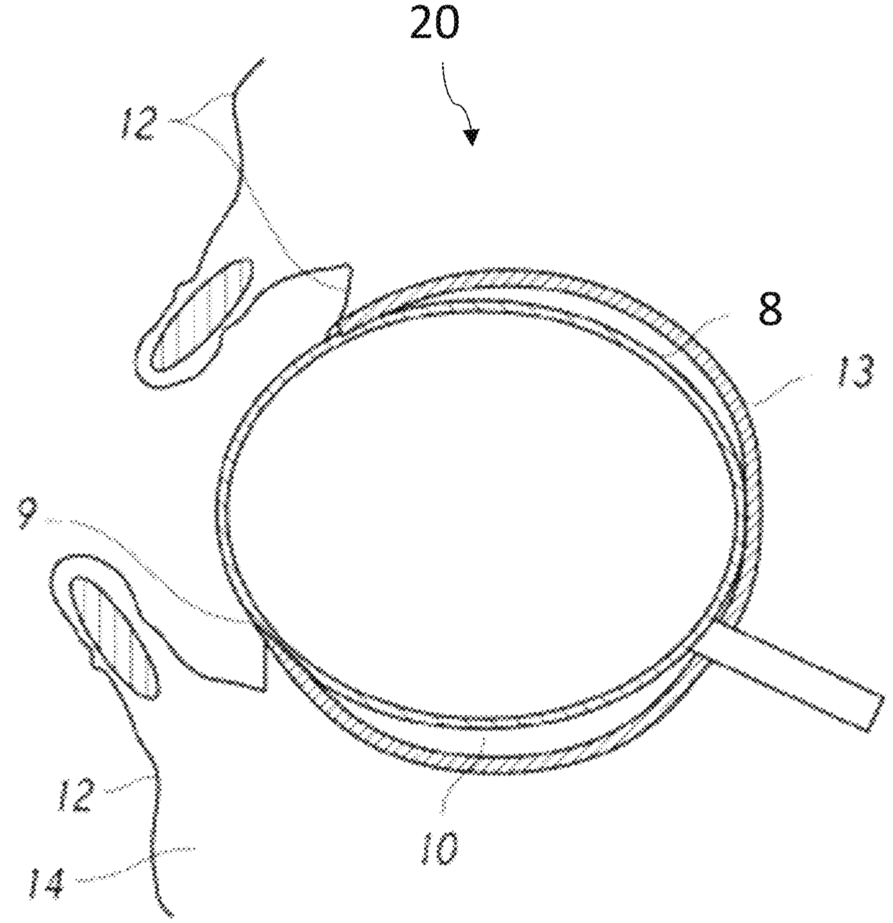
FIG. 2 is another cross-sectional diagram of the human eye, and certain anatomical structures of the eye.

FIG. 2 provides a cross-sectional view of the eye with greater anatomical detail. The conjunctiva 12 is shown in relation to Tenon's capsule 13, a fascial layer of connective tissue that envelops the globe and the extraocular muscles. The anterior attachment of Tenon's capsule occurs at the limbal fusion 9, where the conjunctiva 12 and Tenon's capsule 13 join with the sclera 8. This attachment point is critical for maintaining structural integrity. As shown, Tenon's capsule 13 extends posteriorly until it merges with the dura surrounding the optic nerve. Between the conjunctiva 12 and the sclera 8 lies the subconjunctival space 14, and the space between Tenon's capsule 13 and the sclera 9 is referred to as the intra-Tenon's space 10. These anatomical features are significant for various ocular surgeries, including those involving glaucoma treatments.

In the case of glaucoma, increased pressure within the anterior chamber, caused by an accumulation of aqueous humor, can lead to damage of the optic nerve and the vascular structures at the back of the eye. To manage glaucoma and other conditions that result in elevated intraocular pressure, treatments focus on relieving this pressure to prevent further damage. This is typically achieved by facilitating the drainage of aqueous humor from the anterior chamber, either through natural pathways or surgical intervention.

Spacer Device

Described herein is a spacer device configured for placement in an eye. The spacer device has a size, volume, diameter, length, cross-section and/or shape configured for positioning in an eye, such as a human or animal eye. For example, for subconjunctival, sub-Tenon's or suprachoroidal space implantation.

In some embodiments, when properly placed in the eye, the spacer device can operate as an ocular tissue spacer. In other words, the spacer device can operate as a structure that forms a curved shape and defines a three-dimensional volume (i.e., cavity) between adjacent eye tissue layers or within an eye tissue layer. This creates a dedicated space for drainage, collection, or other fluid management functions.

The term "tissue layer," as used herein, encompasses both a single tissue layer and a collection of layers, such as adjacent stacked layers (a multilayer) or distinct layers. However, the default interpretation typically refers to a single tissue layer. Additionally, when referring to a "tissue layer," it often pertains to a tissue wall characterized by a specific thickness and two sides (outer and inner, or proximal and distal).

In some embodiments, the spacer device can be in fluid communication with one or more eye locations. For example, the spacer device can be configured to receive a fluid therein, such as an intraocular fluid and/or an injected fluid.

In some embodiments, the spacer device can be configured for placement under the conjunctiva or under the Tenon's capsule. The conjunctiva is a thin, transparent membrane covering the white part of the eye (sclera) and the inner eyelids. This placement typically allows easy access for drainage. The Tenon's capsule is a connective tissue layer between the conjunctiva and the sclera. When the ocular tissue spacer is placed under the Tenon's capsule, it is positioned deeper than under the conjunctiva, reducing direct exposure and potentially stabilizing the ocular tissue spacer more securely.

In some embodiments, the spacer device can be in fluid communication with the anterior chamber of the eye, such that the spacer device is configured to receive aqueous humor flowing out of the anterior chamber of the eye, reducing eye internal pressure. Such fluid communication with the anterior chamber can be through an ocular implant, such as a shunt, disposed between the anterior chamber and the spacer device. The ocular implant (e.g., shunt) can form a drainage channel and the spacer device can thus receive aqueous humor flowing out of the anterior chamber of the eye and draining through the ocular implant, reducing eye internal pressure.

When the spacer device is in fluid communication with the anterior chamber of the eye for reducing eye internal pressure, the spacer device can be useful for treatment of glaucoma. This is envisioned to include primary, open-angle glaucoma and secondary, open-angle glaucoma. However, it is conceivable that this spacer device could be used to treat other types of glaucoma, as well as other eye conditions that require the relief of intraocular pressure through the drainage of aqueous humor, such as pigment dispersion syndrome, neovascular glaucoma, uveitic glaucoma, chronic angle closure glaucoma, and pseudoexfoliation syndrome.

Additionally or alternatively, the spacer device can be used to deliver a fluid into the eye, e.g., through a fluid injection. For example, the fluid can be a drug, a therapeutic agent, saline, viscoelastic fluids, and the like. The saline fluid can be used for irrigation. For example, the viscoelastic fluids may comprise hyaluronic acid, chondroitin sulfate, cellulose, derivatives or mixtures thereof, or solutions thereof. In one variation, the viscoelastic fluid comprises sodium hyaluronate. In another variation, the viscoelastic composition may further include a drug. For example, the viscoelastic composition may include a drug suitable for treating glaucoma, reducing or lowering intraocular pressure (IOP), reducing inflammation, and/or preventing infection. Drugs such as an antimetabolite, steroid, heparin, other anticoagulants, and fibrinolytic compounds may also be delivered in combination with the viscoelastic composition. Examples of glaucoma drugs include prostaglandins, beta-blockers, miotics, alpha-adrenergic agonists, or carbonic anhydrase inhibitors. Anti-inflammatory drugs such as corticosteroids or other steroids may be used. For example, steroids such as prednisolone, prednisone, cortisone, cortisol, triamcinolone, or shorter acting steroids may be employed. Examples of antimetabolites include 5-fluorouracil (5-FU) or mitomycin C (MMC). In still another variation, the spacer device is used to deliver the drug alone, without the viscoelastic composition. Saline solution may also be the fluid employed.

In some embodiments, the spacer device may be coated on at least a portion of an internal surface, at least a portion of an external surface, or both, with a biomaterial for increasing surface area and/or reducing irritability. Alternatively, or additionally, the spacer device may be coated on at least a portion of an internal surface, at least a portion of an external surface, or both, with a compound useful for treating ocular hypertension, glaucoma, or pre-glaucoma, infection, or scarring or inflammation postoperatively, and/or with a compound useful for reducing friction thus facilitating insertion in the eye.

In some embodiments, the spacer device can be used in association with antimetabolites and/or in combination with any other anti-scarring, anti-VEGF, or anti-fibrotic agents. When used alongside antimetabolite medications, such as 5-fluorouracil (5-FU) or mitomycin-C (MMC), the device's internal cavity or surrounding surfaces could serve as a vehicle to localize and deliver these antimetabolites agents. The device's three-dimensional structure and position between or within ocular tissues would allow sustained, controlled release of the antimetabolites to the target treatment area.

Alternatively, the spacer device can be implanted without the concurrent use of antimetabolites. In these cases, the device's design and materials can be optimized to minimize inflammatory responses and fibrotic scarring on its own, without the need for additional pharmacological agents.

The spacer device versatile architecture provides multiple surfaces and spaces that could host these supplemental therapies, allowing localized delivery to the surrounding ocular tissues.

Whether used in isolation or as part of a combination treatment approach, incorporating the spacer device into glaucoma or retinal procedures expands the potential therapeutic options. Its ability to integrate drug delivery capabilities alongside its structural spacing and stabilizing functions enhances the device's overall clinical utility.

In some embodiments, the spacer device is solid or semi-solid, and intended for being bio absorbable.

In some embodiments, the spacer device is solid or semi-solid, and intended for being permanent.

In some embodiments, the spacer device can be delivered and placed in the eye with a delivery device configured for ab interno procedures. Alternatively, the spacer device can be delivered and placed with a delivery device configured for ab externo procedures. For example, the spacer device can be delivered and placed in the eye with a delivery device having a delivery member.

In some embodiments, the spacer device can be configured to reversibly transition from a compressed configuration (having a lower profile) to an expanded configuration (having a larger profile). For example, the spacer device can be configured such that the transition from the compressed configuration to the expanded, deployed configuration is immediate or gradual, or where the extent of expansion can be controllable. The transition may occur in multiple discrete steps (i.e., extension of a dimension after the device is in an expanded state), in one-step, or evolve in a continuous fashion where at least one of volume, shape, size, diameter, length, etc. until the desired expansion end point is achieved to accommodate the desired size. For example, a minimum expanded or high-profile state is initially achieved with the option to further expand or extend the high-profile state to accommodate the space requirements.

Advantageously, the compressed configuration facilitates delivery to the implant site. Further, the compressed configuration allows housing and/or translocating the spacer device through the lumen of a delivery member of a delivery device configured to position and deliver the spacer device in the eye.

In some embodiments, the spacer device includes a flexible body configured to conform to anatomical tissue surfaces of the eye. The spacer device can be configured to reversibly transition between a compressed configuration suitable for delivery through a delivery member and an expanded configuration defining a convex, internal three-dimensional volume for receiving fluid from an anterior chamber of the eye. The spacer device can include one or more engaging elements configured to interface with the delivery member to stabilize the spacer device during implantation in the eye.

For example, the flexible body can be configured to be compressed or folded along its longitudinal axis to facilitate insertion through the delivery member.

In some embodiments, the spacer device includes a support structure and at least one deformable member arranged relative to the support structure to define a containment space. For example, the support structure can be configured to define a boundary in a first plane. For example, the support structure and the at least one deformable member can be separate structures in some embodiments or can be a single continuous structure in other embodiments. The support structure and the at least one deformable member are movable between a compressed configuration sized for passage through a lumen, and an expanded configuration. In the expanded configuration, the at least one deformable member extends away from the first plane to define a three-dimensional volume (e.g., cavity) having an apex region spaced from the first plane. The support structure and/or the at least one deformable member is composed of a shape memory material biased toward the expanded configuration. For example, the three-dimensional volume is configured to receive and contain a fluid, when the spacer device is deployed within eye tissue.

In some embodiments, during compression leading to the compressed configuration, the at least one deformable member deforms elastically, collapsing downward toward the plane defined by the support structure. As the device is compressed, the at least one deformable member flattens and aligns substantially parallel to the plane defined by the support structure, while the support structure compresses inwardly to fit within the delivery member lumen. The medical grade material of both the support structure and the at least one deformable member allows for significant elastic deformation without plastic deformation or loss of shape memory. When compressed, the support structure deforms into an elongated shape, allowing the entire device to achieve a compressed profile that fits within the delivery member lumen, which can have a relatively small inner diameter. The inherent spring force of the materials maintains sufficient outward bias during compression to ensure reliable self-expansion upon deployment, while remaining below the materials' elastic limit to prevent fatigue or permanent deformation through multiple compression-expansion cycles, for example.

In some embodiments, the spacer device can be self-expanding or adjustably expandable depending on the extent of spacing that is required in the eye tissue.

In some embodiments, the spacer device includes tissue interface features associated with the support structure. These tissue interface features can incorporate specific tissue-engaging elements to help anchor the device in the desired location within the eye after deployment. For example, the spacer device can be stabilized in position using tissue-engaging elements, such as hooks, miniature tacks, or suture points, extending from the tissue interface features of the support structure. Alternatively, the tissue-engaging elements may comprise small protrusions, barbs, or other surface irregularities that are able to lightly grip or catch on the surrounding ocular tissues. This helps prevent unwanted migration or displacement of the device once it has been placed in the targeted position. Alternatively, the tissue interface features could include eyelets or other mounting points to allow suturing of the device in place. This provides a more secure fixation method compared to relying solely on frictional engagement of the tissue-engaging elements with the tissues.

Incorporating these tissue-engaging elements as part of the overall tissue interface features on the support structure ensures the spacer device remains stably positioned and contained within the eye, even with any normal eye movements or fluid dynamics. This enhances the reliable performance and therapeutic efficacy of the deployed device.

In some embodiments, the spacer device can be further configured to include a port for receiving or fluidly connecting to an ocular implant (e.g., shunt). This port can be in fluid communication with the three-dimensional volume.

In some embodiments, the spacer device can be used with a reduced width and increased height profile to be positioned within the suprachoroidal space, using a curved ab interno delivery cannula. This could serve to both lower intraocular pressure as well as provide a depot for drug delivery. At the suprachoroidal space, the scleral thickness is approximately 0.5 mm, thus a delivery member length of at least 0.5 mm to 1.2 mm could administer hypotensive medications, anti-inflammatory agents (such as steroids), or gene therapies for retinal dystrophies, wet age-related macular degeneration (AMD), or diabetic maculopathy, for example.

By transitioning the device to a taller, more elongated configuration, it can be effectively delivered and contained within the suprachoroidal space using a minimally invasive ab interno approach. This positioning allows the device to create a pathway for aqueous outflow to reduce intraocular pressure, while also providing a protected microenvironment to serve as a drug delivery depot.

The increased height of the device in this configuration, compared to its wider footprint in the previous placements, accommodates the relatively thin scleral tissue thickness in the suprachoroidal space. Needle lengths in the 0.5-1.2 mm range would be sufficient to penetrate the sclera and position therapeutic agents near the targeted ocular structures.

Utilizing the spacer device in this suprachoroidal drug delivery application leverages its versatile design and ability to adapt its dimensional profile to access different ocular tissue planes. This expands the potential clinical utility of the device beyond just providing a mechanical spacing function.

In non-limiting implementations, the device can be used in combination with a trabeculectomy procedure. Trabeculectomy is a surgical procedure used to treat glaucoma by relieving intraocular pressure (IOP) within the eye. It involves creating a small flap in the sclera (the white outer layer of the eyeball) and making an opening under it to allow excess aqueous humor (fluid) to drain from inside the eye to a space underneath the conjunctiva (the clear tissue covering the white part of the eye). This drainage reduces the pressure on the optic nerve, helping to prevent further vision loss. Trabeculectomy is often recommended when medications or laser treatments do not adequately control IOP. Alternatively, the device can be used alongside an ab externo or ab interno implant to drain fluid from the anterior chamber to the outside of the anterior chamber, under the conjunctiva or Tenon's membrane.

When used with a trabeculectomy, the spacer device can be positioned to occupy the surgically created fistula, helping to maintain the patency of the outflow pathway. Its self-expanding three-dimensional structure will fill the space and prevent closure, while still allowing aqueous flow through the device's internal volume or around its perimeter.

In a separate application, the spacer device could be implanted in conjunction with a drainage implant that shunts fluid from the anterior chamber to the subconjunctival or sub-Tenon's space. The device's tissue-engaging elements could help stabilize the position of the drainage implant, while its cavity could integrate with the outflow pathway to facilitate aqueous humor evacuation.

Regardless of whether used with a trabeculectomy or a drainage implant, the versatile design of the spacer device allows it to be tailored to complement the specific surgical technique. Its ability to transition between compressed and expanded configurations, as well as customize the dimensional profile, enables it to be effectively combined with other glaucoma interventions to enhance their performance and durability.

The device's unique geometry as described herein, enables it to function effectively in controlled environments where precise containment, fluid distribution, or structural support is required.

First Implementation

Figure 3:
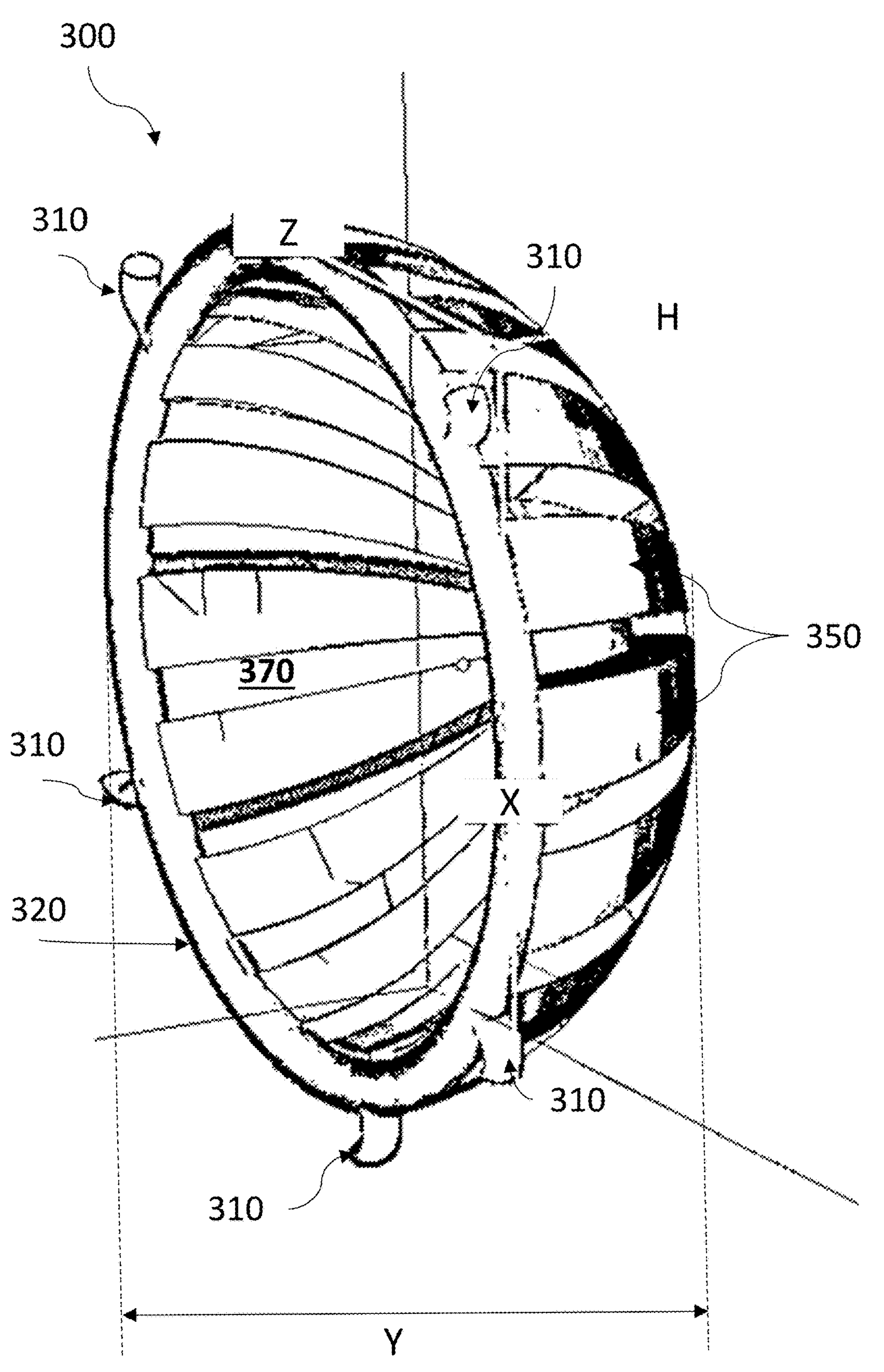
FIG. 3 is a non-limiting perspective side view of a first implementation of a spacer device for deployment within an eye, in an expanded configuration, in accordance with non-limiting embodiments of the present disclosure.

FIG. 3 illustrates a first non-limiting implementation of a spacer device that is arranged and configured in accordance with certain features, aspects, and advantages of the present disclosure.

In some embodiments, the spacer device 300 can be configured to reversibly transition from a first, compressed configuration (having a lower profile) to a second, expanded configuration (having a larger profile). For example, the spacer device 300 can have self-expandable characteristics and is reversibly movable from the compressed configuration to the expanded configuration, and vice versa.

In some embodiments, the spacer device 300 is configured to reversibly transition between the compressed configuration, sized to fit within at least a portion of the delivery member 400, and the expanded configuration.

In some embodiments, the spacer device 300 includes a support structure 320. For example, the support structure 320 may be composed of a single wire-structure capable of expanding into the expanded configuration, as a deployed loop frame.

In some embodiments, the support structure 320 can be a wire having a round cross section of sufficient diameter to reduce the likelihood of tearing or damaging eye structures when delivering and placing the spacer device 300 in the eye. The diameter of that round cross section wire may be of from about 0.02 mm to about 0.7 mm, but may also be any size that prevents excessive stress from being placed in the eye. Alternatively, the profile of the support structure 320 may be ovular with a larger width or height, or may be a strap.

In some embodiments, the deployed loop has a perimeter defining a circular, oval or other atraumatic cross-section internal area. The internal area may have any size that is suitable for delivery and placement of the spacer device 300 in the eye, without damaging structures of the eye or causing significant discomfort to the patient.

For example, the deployed loop can have a perimeter defining a circular cross-section internal area.

Figure 4:
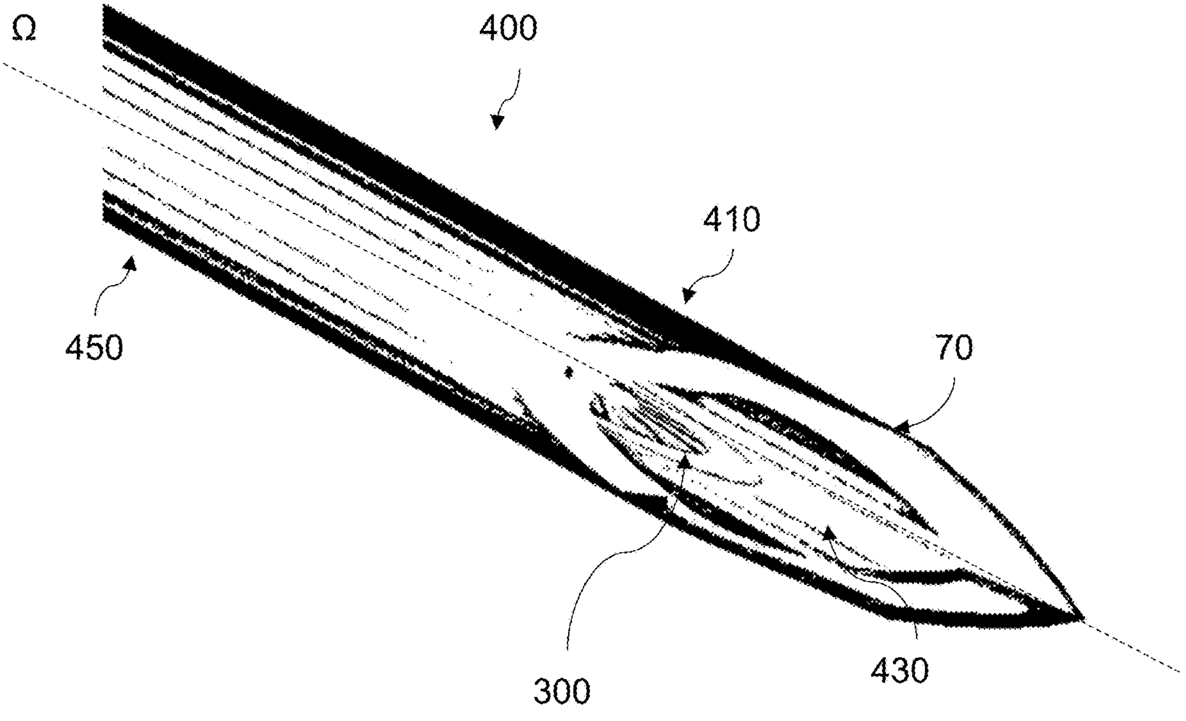
FIG. 4 is a non-limiting perspective side view of a distal end of a delivery member which houses the spacer device of FIG. 3 in a compressed configuration, in accordance with non-limiting embodiments of the present disclosure.

In some embodiments, when the spacer device 300 is in the compressed configuration, the support structure 320 is in a compressed configuration. For example, the support structure 320 in the compressed configuration forms a collapsed loop with a reduced internal area. For example, the collapsed loop may have an ellipse shape that is elongated compared to that one of the deployed loop. In use, the support structure 320 in the compressed configuration may have a size that allows it to fit within the lumen of a delivery member 400, as shown in FIG. 4. Depending upon the material used to fabricate the support structure 320, the support structure 320 may have a degree of stiffness in the compressed configuration such that it may be directly insertable and pushable through the delivery member 400.

In some embodiments, the support structure 320 is configured to transition between the compressed configuration, sized to fit within at least a portion of the delivery member 400, and the expanded configuration.

In some embodiments, the support structure 320 is composed of a medical grade material suitable for use in the eye. For example, the support structure 320 can include a material allowing it to transition from the compressed configuration to the expanded configuration, with an amount of elasticity. For example, the support structure 320 can be made of nitinol (nickel-titanium alloy), Magnesium alloys, polyamide, polyimide, silicone, or any suitable shape memory polymer, such as Polyethylene Terephthalate (PET), Polytetrafluoroethylene (PTFE), Polyetheretherketone (PEEK), Polylactic Acid (PLA), Polycaprolactone (PCL), Polyurethanes, Polyhydroxybutyrate (PHB), Chitosan, Silk fibroin, Polydioxanone (PDO), or any composite thereof.

In some embodiments, the spacer device 300 further includes at least one deformable member 350. For example, the at least one deformable member 350 can be arranged relative to the support structure 320 to define a three-dimensional volume.

In some embodiments, when the spacer device self-expands upon deployment, the at least one deformable member 350 self-expands from its compressed configuration and extends from the support structure 320 to form the three-dimensional volume—e.g., projecting in an arcuate or curved manner relative to the plane formed by the support structure 320. This expansion can form a dome-shaped structure that arches above the plane, thereby creating a defined three-dimensional volume (e.g., cavity) between the apex of the dome and the plane of the support structure 320. The at least one deformable member 350 can curve upwardly from its connections to the frame 320, extending in a direction substantially perpendicular to the base plane at its points of connection, and then curve inwardly toward a central axis of the device 300 that is perpendicular to the plane formed by the support structure 320. The at least one deformable member 350 maintains its curved configuration due to its inherent spring force, thereby forming and maintaining the three-dimensional cavity structure suitable for receiving and containing fluid, while allowing the device 300 to be compressed for delivery through the delivery member 400. This three-dimensional volume is configured to receive and contain a fluid, facilitating a therapeutic or structural purpose within the eye. The at least one deformable member is strategically positioned to maintain the dome shape, providing structural integrity to the three-dimensional volume when the device is fully deployed.

Alternatively, the at least one deformable member 350 joins with a periphery of a top annular element (not shown), which is in opposite and distant relationship relative to the support structure 320 when the spacer device 300 is in the expanded configuration. For example, the top annular element can have a perimeter defining a substantially circular or oval cross-section, corresponding to the cross-section shape of the support structure 320 open area.

Figure 5:
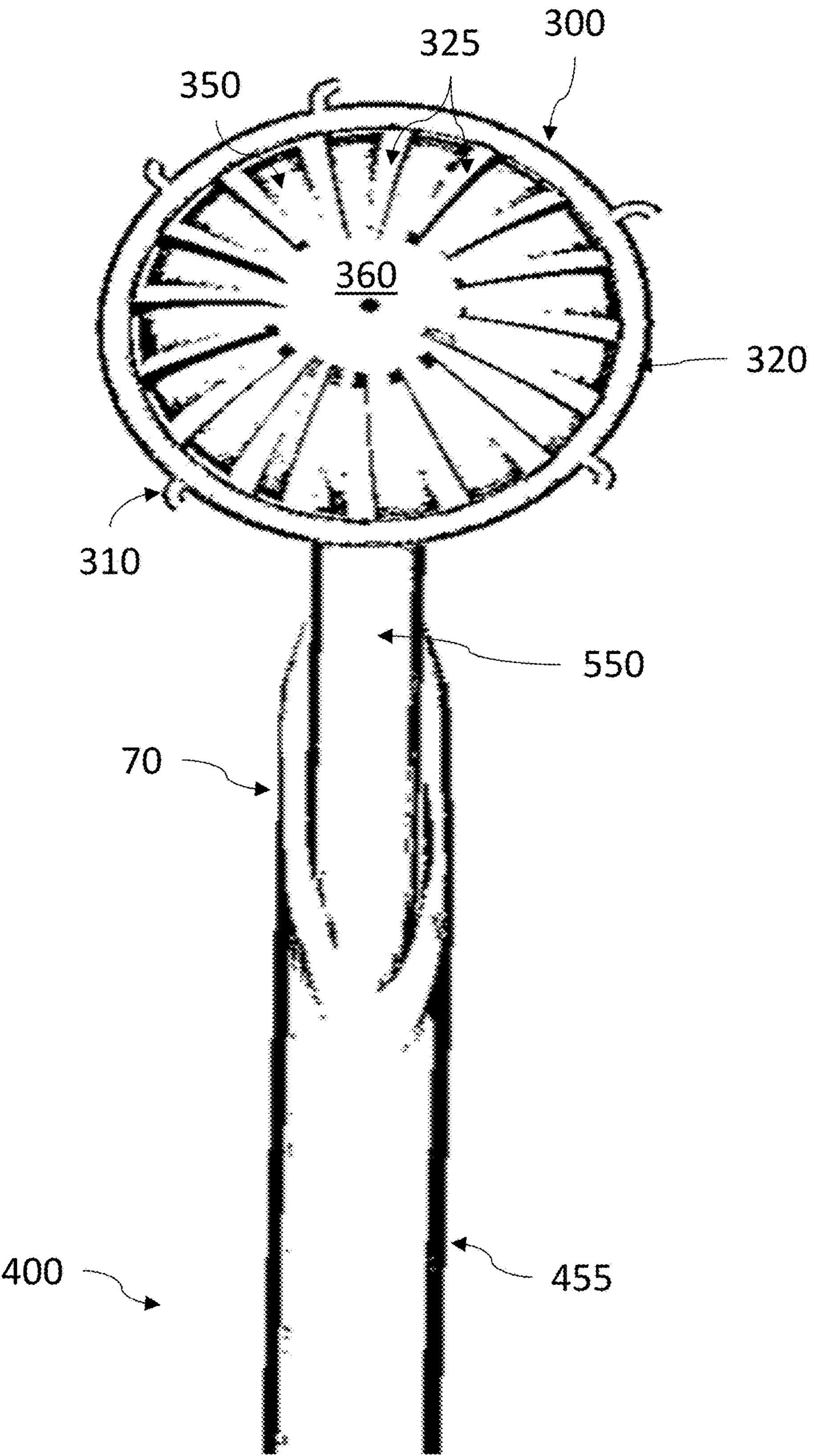
FIG. 5 is a non-limiting top view of a distal end of a delivery member with the spacer device of FIG. 3 deployed therefrom and in an expanded configuration, in accordance with non-limiting embodiments of the present disclosure.

Alternatively, the at least one deformable member 350 couples with the periphery of a top plate 360, as shown in FIG. 5, which is in opposite and distant relationship relative to the support structure 320 when the spacer device 300 is in the expanded configuration. For example, the top plate 360 can have a substantially circular or oval cross-section, corresponding to the cross-section shape of the support structure 320 open area.

In some embodiments, when the spacer device 300 is in the compressed configuration, the at least one deformable member 350 is compressed allowing the spacer device 300 to be contained (housed) within the delivery member 400. In other words, the at least one deformable member 350 can substantially form a compacted structure with the support structure 320 to enable for the spacer device 300 to be contained (housed) within a lumen of the delivery member 400. During compression for delivery, the at least one deformable member 350 deform elastically, collapsing downward toward the base plane defined by the support structure 320. As the device 300 is compressed, the at least one deformable member 350 flatten and align substantially parallel to the base plane, while the support structure 320 compresses inwardly to fit within the delivery member 400 lumen. The medical grade material of both the frame 320 and deformable members 350 allows for significant elastic deformation without plastic deformation or loss of shape memory. When compressed, the frame 320 deforms into an elongated shape, allowing the entire device 300 to achieve a compressed profile that fits within a delivery member 400 having a relatively small inner diameter lumen. The inherent spring force of the materials maintains sufficient outward bias during compression to ensure reliable self-expansion upon deployment, while remaining below the materials' elastic limit to prevent fatigue or permanent deformation through multiple compression-expansion cycles, for example.

In some embodiments, the spacer device 300 is designed such that the support structure 320 defines a peripheral boundary and base plane, with the at least one deformable member 350 extending outwards and away from this plane to create the three-dimensional volume, as shown in FIG. 3. For example, the at least one deformable member 350 can self-expand from their compressed state and project in an arcuate or dome-like manner relative to the plane formed by the support structure 320. This expansion forms a dome-shaped structure that arches above the plane, thereby creating a defined cavity between the apex of the dome and the plane of the frame. This cavity is configured to receive and contain a fluid, facilitating a therapeutic or structural purpose within the eye. The at least one deformable member 350 are strategically positioned to maintain the dome shape, providing structural integrity to the cavity when the device is fully deployed.

Such transition can be obtained with a self-expansion characteristic of the spacer device 300.

In some embodiments, the at least one deformable member 350 are composed of a medical grade material suitable for use in the eye. For example, the at least one deformable member 350 can include a material allowing these to transition from the compressed configuration to the expanded configuration, with an amount of elasticity. For example, the at least one deformable member 350 can be formed from any suitable material, including but not limited to metals, polymers, elastomers, hydrogels, smart materials, or composites thereof. For example, suitable metals include shape memory alloys such as Nitinol (nickel-titanium alloy), copper-aluminum-nickel alloys, and iron-based shape memory alloys. Suitable polymers include polyamide, polyimide, polyethylene terephthalate (PET), polytetrafluoroethylene (PTFE), polyetheretherketone (PEEK), polylactic acid (PLA), polycaprolactone (PCL), polyurethanes, polyhydroxybutyrate (PHB), chitosan, polydioxanone (PDO), silk fibroin, acrylic polymers, and thermoplastic or thermoset materials. For example, polyurethanes include thermoplastic polyurethane (TPU), medical-grade polyether urethane, and silicone-polyurethane copolymers. For example, acrylic polymers include hydrophobic acrylic, hydrophilic acrylic, and crosslinked copolymers of methacrylate and acrylate derivatives. Elastomeric materials may also be used, such as silicone-based elastomers. For example, silicone-based elastomers include polydimethylsiloxane (PDMS), crosslinked medical-grade silicone, and room temperature vulcanizing (RTV) silicone. Hydrogels may be used, including but not limited to poly (2-hydroxyethyl methacrylate) (PHEMA), polyacrylamide-based hydrogels, polyvinyl alcohol (PVA) hydrogel, collagen-hydrogel copolymers, and polyethylene glycol (PEG)-based hydrogels. Smart or stimuli-responsive polymers may also be used, including thermoresponsive and shape memory polymers. For example, thermoresponsive include poly(N-isopropylacrylamide) (PNIPAM), poly(N-vinylcaprolactam) (PVCL), and poly(ethylene glycol)-based block copolymers. Biodegradable polymers with form retention properties may also be used. For example, such biodegradable polymers include poly(lactic-co-glycolic acid) (PLGA), polycaprolactone (PCL), polydioxanone (PDO), and poly(L-lactic acid) (PLLA). Other suitable materials may include magnesium alloys, Collamer (hydroxyethyl methacrylate with porcine collagen), polyHEMA-collagen copolymers, acrylic-urethane hybrids, or any biocompatible composite or combination thereof.

In some embodiments, there is a spacing 325 between each adjacent deformable members 350, where each of the respective spacing 325 extends along an edge of the respective expandable member 350, as shown in FIG. 5. Such spacing 325 can contribute to the flexibility characteristics of the spacer device 300, thus allowing the reversible transition from the expanded to the compressed configurations.

Second Implementation

FIG. 6A to FIG. 7B and FIG. 9K and FIG. 9L illustrate a second non-limiting implementation of a spacer device that is arranged and configured in accordance with certain features, aspects, and advantages of the present disclosure.

In some embodiments, the spacer device 700 can be configured to reversibly transition from a first, compressed configuration (having a lower profile) to a second, expanded configuration (having a larger profile). For example, the spacer device 700 can have self-expandable characteristics and is reversibly movable from the compressed configuration to the expanded configuration, and vice versa.

In some embodiments, the spacer device 700 is configured to reversibly transition between the compressed configuration, sized to fit within at least a portion of the delivery member 400, and the expanded configuration.

Figure 9A:
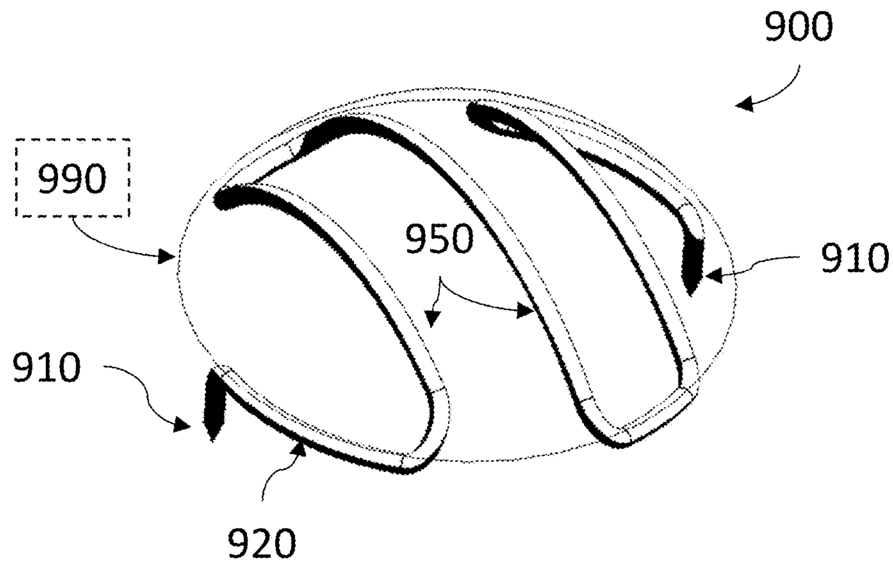
FIG. 9A is a non-limiting perspective view of a variant of the spacer device of FIG. 8, in accordance with non-limiting embodiments of the present disclosure.
Figure 9B:
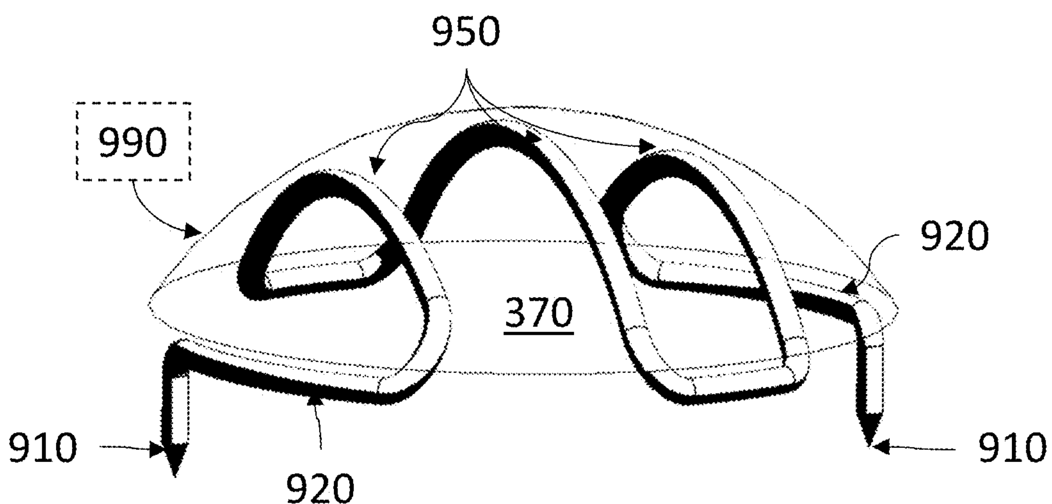
FIG. 9B is a non-limiting perspective side view of the spacer device of FIG. 9A, in accordance with non-limiting embodiments of the present disclosure.
Figure 9C:
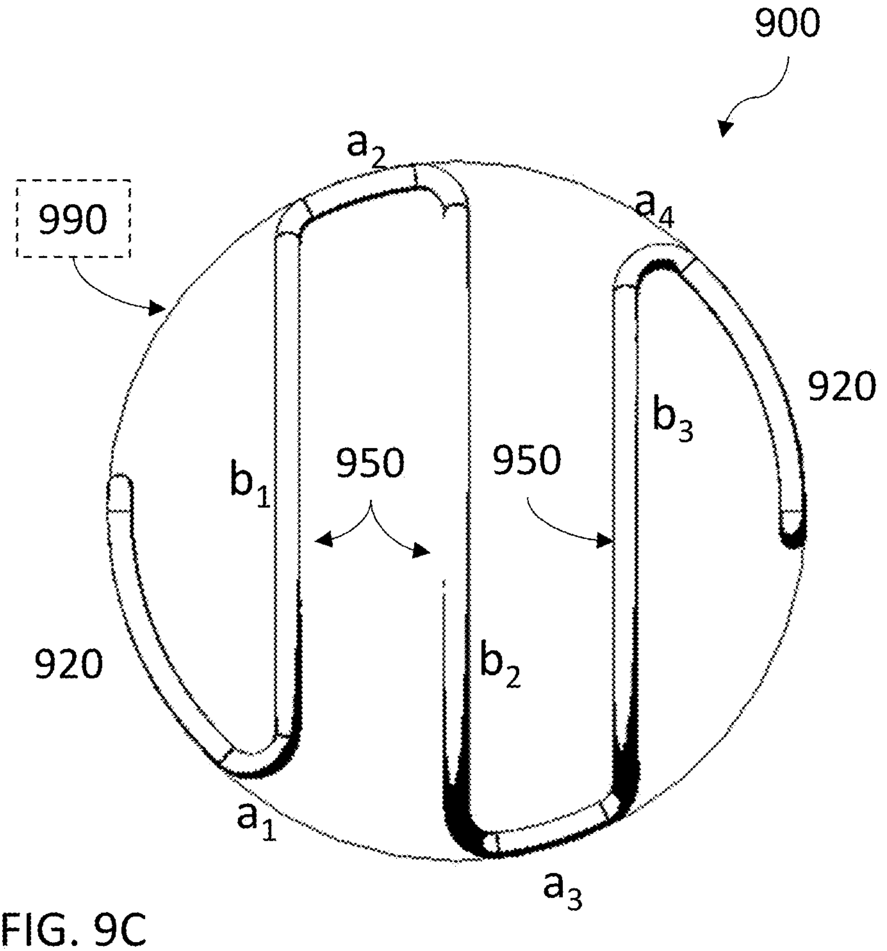
FIG. 9C is a non-limiting top view of the spacer device of FIG. 9A, in accordance with non-limiting embodiments of the present disclosure.
Figure 9D:
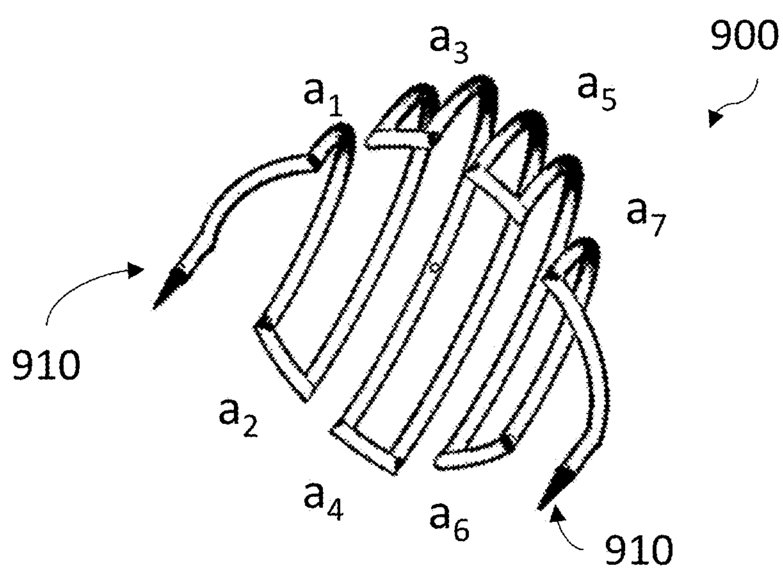
FIG. 9D is a non-limiting bottom perspective view of a variant of the spacer device of FIG. 8, in accordance with non-limiting embodiments of the present disclosure.
Figure 9E:
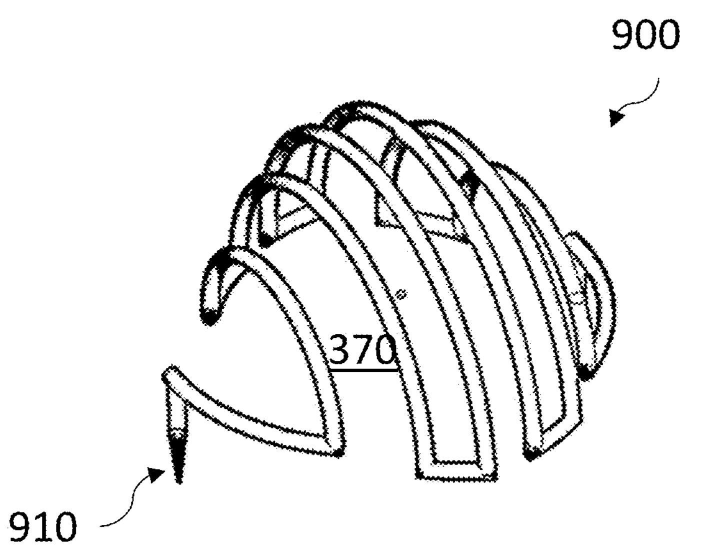
FIG. 9E is a non-limiting elevated perspective view of the spacer device of FIG. 9D, in accordance with non-limiting embodiments of the present disclosure.

In some embodiments, the spacer device 700 includes a support structure 720. For example, the support structure 720 may be composed of a single wire-structure capable of expanding into the expanded configuration as a deployed loop to form the dome shape, as shown in FIG. 9K and FIG. 9L. For example, the single wire-structure can form concentric, circular rings arranged in a concentric configuration, where the single wire-structure forms a continuous ring that increases in diameter from a central region toward the peripheral boundary.

In some embodiments, the support structure 720 can be a wire having a round cross section of sufficient diameter to reduce the likelihood of tearing or damaging eye structures when delivering and placing the spacer device 700 in the eye. The diameter of that round cross section wire may be of from about 0.02 mm to about 0.7 mm, but may also be any size that prevents excessive stress from being placed in the eye. Alternatively, the profile of the support structure 720 may be ovular with a larger width or height, or may be a strap.

In some embodiments, the deployed loop has a perimeter defining a circular, oval or other atraumatic cross-section internal area. The internal area may have any size that is suitable for delivery and placement of the spacer device 700 in the eye, without damaging structures of the eye or causing significant discomfort to the patient.

For example, the deployed loop can have a perimeter defining a circular cross-section internal area.

In some embodiments, when the spacer device 700 is in the compressed configuration, the support structure 720 forms a collapsed loop with a reduced internal area. For example, the collapsed loop frame 720 may have an ellipse shape which is elongated compared to that one of the deployed loop. In use, the collapsed loop may have a size and shape that allows it to be contained (housed) within the delivery member 400 of a suitable spacer device, similar to spacer device 300. Depending upon the material used to fabricate the support structure 720, the support structure 720 may have a degree of stiffness in the compressed configuration such that it may be directly insertable and pushable through the delivery member 400.

In some embodiments, the support structure 720 is configured to transition between the compressed configuration, sized to fit within at least a portion of the delivery member 400, and the expanded configuration.

In some embodiments, the support structure 720 is composed of a medical grade material suitable for use in the eye. For example, the support structure 720 can include a material allowing it to transition from the compressed configuration to the expanded configuration, with an amount of elasticity. For example, the support structure 720 can be made of nitinol (nickel-titanium alloy), Magnesium alloys, polyamide, polyimide, silicone, or any suitable shape memory polymer, such as Polyethylene Terephthalate (PET), Polytetrafluoroethylene (PTFE), Polyetheretherketone (PEEK), Polylactic Acid (PLA), Polycaprolactone (PCL), Polyurethanes, Polyhydroxybutyrate (PHB), Chitosan, Silk fibroin, Polydioxanone (PDO), or any composite thereof.

Figure 6A:
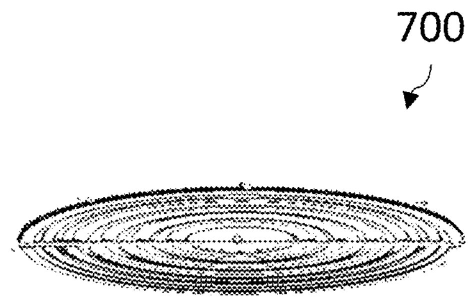
FIG. 6A is a non-limiting perspective side view of a second implementation of a spacer device for deployment within an eye, in a compressed configuration, in accordance with non-limiting embodiments of the present disclosure.
Figure 6B:
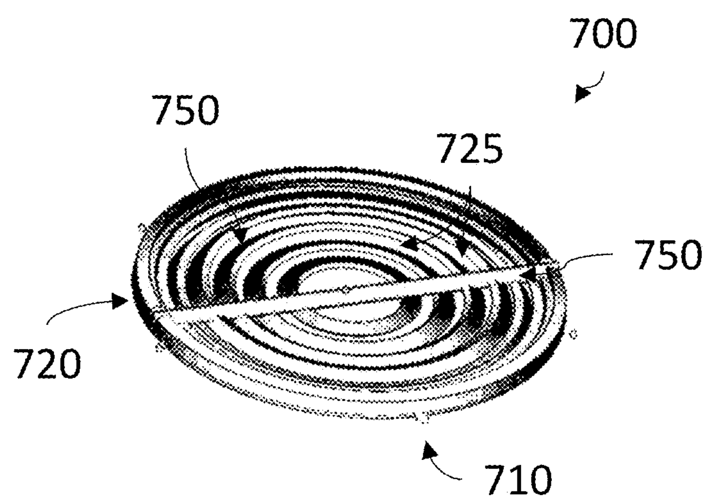
FIG. 6B is a non-limiting perspective elevated view of the spacer device of FIG. 6A, in accordance with non-limiting embodiments of the present disclosure.

In some embodiments, the spacer device 700 further includes at least one deformable member 750, as shown in FIG. 6B. For example, the at least one deformable member 750 can be arranged relative to the support structure 720 to define a three-dimensional volume in the expanded configuration.

In some embodiments, the at least one deformable member 750 extends on one side of a plane formed by the support structure 720.

In some embodiments, the at least one deformable member 750 can include concentric, circular rings arranged in a spaced-apart configuration. For example, the at least one deformable member 750 can form an open, grid-like surface that defines the spacer device 700 contour. In the expanded configuration, the spacer device 700 forms a three-dimensional volume defined by the at least one deformable member 750 and support structure 720.

In some embodiments, the concentric, circular rings are arranged in a concentric configuration, with each member 750 forming a continuous ring that increases in diameter from a central region toward the peripheral boundary defined by the support structure 720. The concentric, circular rings extend away from the support structure 720 to create an apex region spaced from the plane formed by the support structure 720. This arch-like expansion of the at least one deformable member 750 forms an enclosed cavity or volume capable of receiving and containing a fluid. The inherent spring force and shape memory of the at least one deformable member 750 allows the self-expansion from a compressed configuration into this three-dimensional expanded configuration when the constraining forces are removed upon deployment from the delivery member 400 lumen.

In some embodiments, each of the at least one deformable member 750 can be coupled to the support structure 720. For example, such coupling can be via an indirect coupling through one or more support members 780, as shown in FIG. 6A to FIG. 7B. For example, the one or more support members 780 can be one or more arcuate support bars extending radially from a first outer edge of the support structure 720 to a second outer edge of the support structure 720, the first and second edges being in opposite relationship one to another. The one or more support members 780 can extend radially from the first to the second outer edges of the support structure 720 and extend through a central region of the support structure 720. As shown in FIG. 6A to FIG. 7B, the spacer device 700 can include a single support member 780.

Figure 7A:
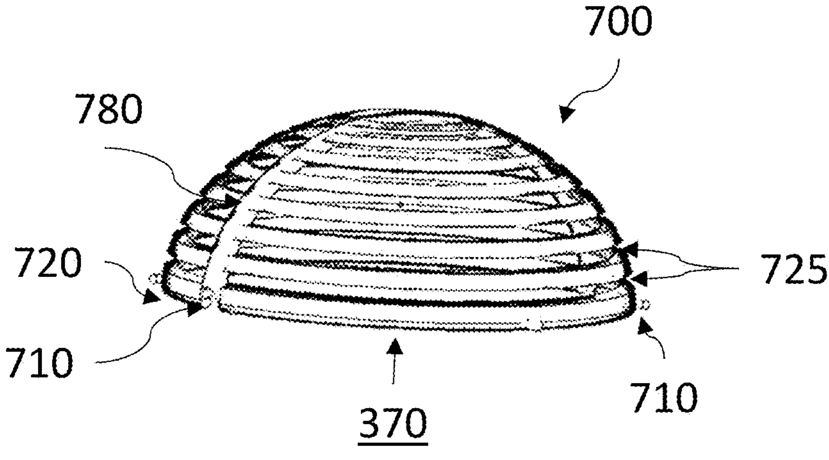
FIG. 7A is a non-limiting perspective side view of the spacer device of FIG. 6A, in an expanded configuration, in accordance with non-limiting embodiments of the present disclosure.
Figure 7B:
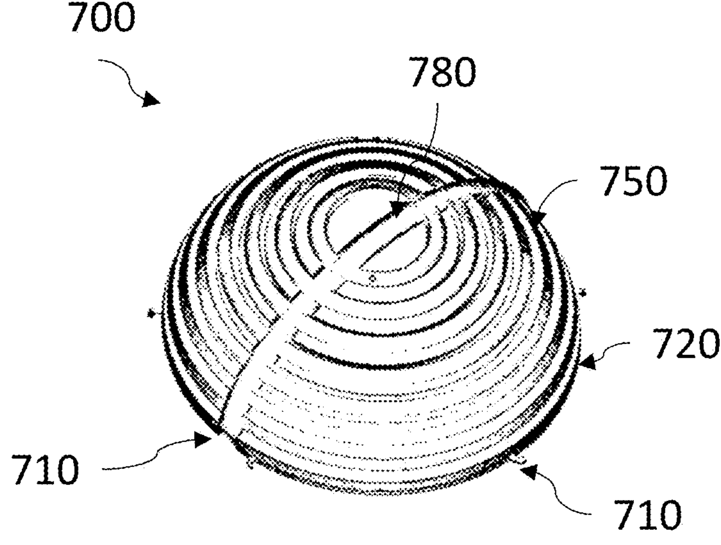
FIG. 7B is a non-limiting perspective elevated view of the spacer device of FIG. 7A, in accordance with non-limiting embodiments of the present disclosure.

In some embodiments, the spacer device 700 is capable of transitioning from the expanded configuration shown in FIG. 7A and FIG. 7B, forming a dome-shape, to the compressed configuration shown in FIG. 6A and FIG. 6B, forming a planar disk shape by compressing the concentric deformable members 750 and the one or more support members 780 along an axis perpendicular to the plane of the support structure 720.

In some embodiments, when the spacer device 700 is in the compressed configuration, the at least one deformable member 750 are compressed allowing the spacer device 700 to be contained (housed) within the delivery member 400. In other words, the at least one deformable member 750 can substantially form a compacted structure with the support structure 720 to enable for the spacer device 700 to be contained (housed) within a lumen of the delivery member 400. To facilitate delivery through a small lumen, the spacer device is in a compressed configuration. In the compressed state, the at least one deformable member 750 nest concentrically, aligning substantially parallel to the support structure 720 and decreasing in diameter toward the central region. The support structure 720 also deforms to a narrower profile. This compression causes the overall height and width of the device 700 to be reduced, allowing it to fit within the lumen of a delivery instrument shaft 400. For example, the elastic properties of the at least one deformable member 750 and base structure 720 enable this compression without plastic deformation, ensuring the device can reliably self-expand back to the desired three-dimensional volume upon deployment and release of the constraining forces.

In some embodiments, when the spacer device 700 transitions to the expanded configuration, the at least one deformable member 750 extends away from a plane formed by the support structure 720, as shown in FIG. 7A and FIG. 7B. Such transition can be obtained with a self-expansion characteristic of the spacer device 700.

Figure 8A:
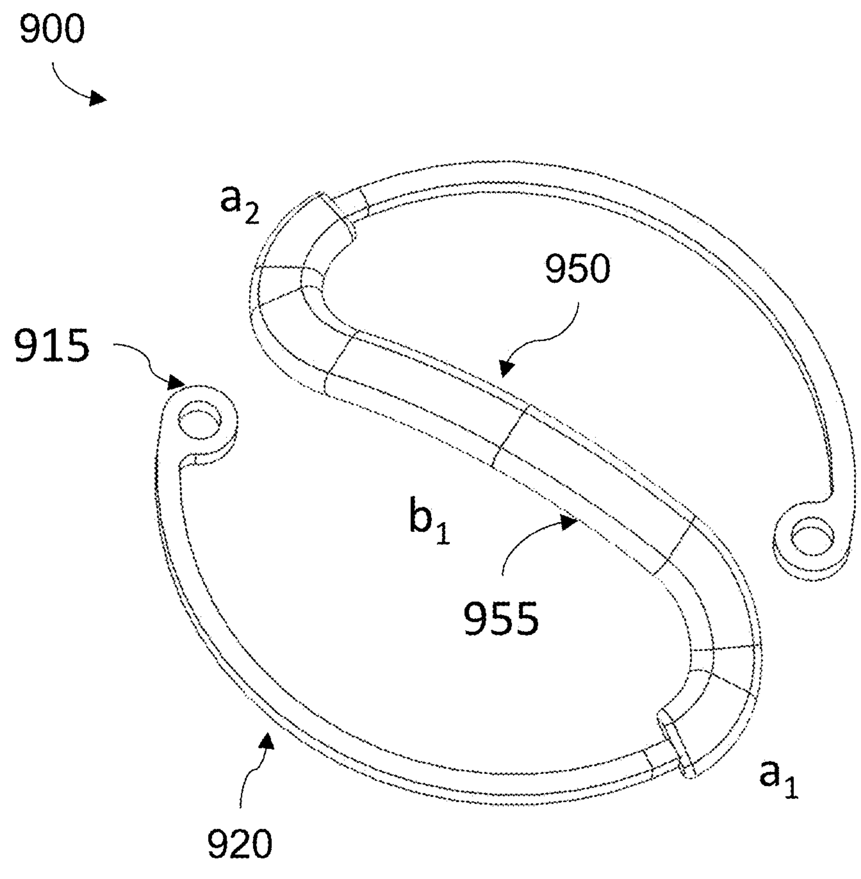
FIG. 8 third implementation of a spacer device for deployment within an eye, in an expanded configuration, in accordance with non-limiting embodiments of the present disclosure
Figure 8B:
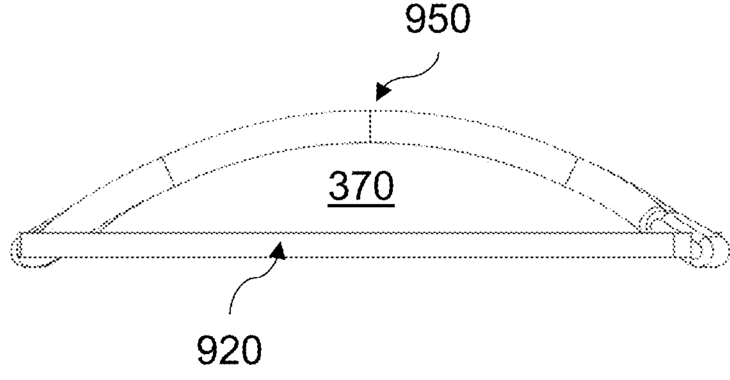

In some embodiments, the spacer device 700 is capable of forming a dome structure when in the expanded configuration, as shown in FIG. 7A and FIG. 8B.

Such transition can be obtained with a self-expansion characteristic of the spacer device 700.

In some embodiments, the at least one deformable member 750 and/or support members 780 are composed of a medical grade material suitable for use in the eye. For example, the at least one deformable member 750 and/or support members 780 can include a material allowing these to transition from the compressed configuration to the expanded configuration, with an amount of elasticity. For example, the at least one deformable member 750 and/or support members 780 can be can be formed from any suitable material, including but not limited to metals, polymers, elastomers, hydrogels, smart materials, or composites thereof. For example, suitable metals include shape memory alloys such as Nitinol (nickel-titanium alloy), copper-aluminum-nickel alloys, and iron-based shape memory alloys. Suitable polymers include polyamide, polyimide, polyethylene terephthalate (PET), polytetrafluoroethylene (PTFE), polyetheretherketone (PEEK), polylactic acid (PLA), polycaprolactone (PCL), polyurethanes, polyhydroxybutyrate (PHB), chitosan, polydioxanone (PDO), silk fibroin, acrylic polymers, and thermoplastic or thermoset materials. For example, polyurethanes include thermoplastic polyurethane (TPU), medical-grade polyether urethane, and silicone-polyurethane copolymers. For example, acrylic polymers include hydrophobic acrylic, hydrophilic acrylic, and crosslinked copolymers of methacrylate and acrylate derivatives. Elastomeric materials may also be used, such as silicone-based elastomers. For example, silicone-based elastomers include polydimethylsiloxane (PDMS), crosslinked medical-grade silicone, and room temperature vulcanizing (RTV) silicone. Hydrogels may be used, including but not limited to poly (2-hydroxyethyl methacrylate) (PHEMA), polyacrylamide-based hydrogels, polyvinyl alcohol (PVA) hydrogel, collagen-hydrogel copolymers, and polyethylene glycol (PEG)-based hydrogels. Smart or stimuli-responsive polymers may also be used, including thermoresponsive and shape memory polymers. For example, thermoresponsive polymers include poly(N-isopropylacrylamide) (PNIPAM), poly(N-vinylcaprolactam) (PVCL), and poly(ethylene glycol)-based block copolymers. Biodegradable polymers with form retention properties may also be used. For example, such biodegradable polymers include poly(lactic-co-glycolic acid) (PLGA), polycaprolactone (PCL), polydioxanone (PDO), and poly(L-lactic acid) (PLLA). Other suitable materials may include magnesium alloys, Collamer (hydroxyethyl methacrylate with porcine collagen), polyHEMA-collagen copolymers, acrylic-urethane hybrids, or any biocompatible composite or combination thereof.

In some embodiments, there is a spacing 725 between each adjacent deformable members 750, where each of the respective spacing 725 extends along an edge of the respective expandable member 750, as shown in FIG. 7A and FIG. 7B. Such spacing 825 can contribute to the flexibility characteristics of the spacer device 700, thus allowing the reversible transition from the expanded to the compressed configurations.

Third Implementation

FIG. 8A to FIG. 9P illustrate a third non-limiting implementation of a spacer device that is arranged and configured in accordance with certain features, aspects, and advantages of the present disclosure.

In some embodiments, the spacer device 900 can be configured to reversibly transition from a first, compressed configuration (having a lower profile) to a second, expanded configuration (having a larger profile). For example, the spacer device 900 can have self-expandable characteristics and is reversibly movable from the compressed configuration to the expanded configuration, and vice versa.

In some embodiments, the spacer device 900 is configured to reversibly transition between the compressed configuration, sized to fit within at least a portion of the delivery member 400, and the expanded configuration.

In some embodiments, the spacer device 900 includes a support structure 920. For example, the support structure 920 may be composed of a single wire-structure capable of expanding into the expanded configuration. Depending upon the material used to fabricate the support structure 920, the support structure 920 may have a degree of stiffness in the compressed configuration such that it may be directly insertable and pushable through the delivery member 400.

In some embodiments, the support structure 920 is composed of a medical grade material suitable for use in the eye. For example, the support structure 920 can include a material allowing it to transition from the compressed configuration to the expanded configuration, with an amount of elasticity. For example, the support structure 920 can be made of nitinol (nickel-titanium alloy), Magnesium alloys, polyamide, polyimide, silicone, or any suitable shape memory polymer, such as Polyethylene Terephthalate (PET), Polytetrafluoroethylene (PTFE), Polyetheretherketone (PEEK), Polylactic Acid (PLA), Polycaprolactone (PCL), Polyurethanes, Polyhydroxybutyrate (PHB), Chitosan, Silk fibroin, Polydioxanone (PDO), or any composite thereof. Preferably, the support structure 920 is composed of nitinol.

In some embodiments, the support structure 920 is configured to transition between the compressed configuration, sized to fit within at least a portion of the delivery member 400, and the expanded configuration.

In some embodiments, the support structure 920 includes at least one deformable member 950. For example, the at least one deformable member 950 can be arranged relative to the support structure 920 to define a three-dimensional volume in the expanded configuration.

In some embodiments, the at least one deformable member 950 extends from the support structure 920. For example, the support structure 920 and the at least one deformable member 950 can be composed of a single wire. In the expanded configuration, the spacer device 900 can form a curved shape. For example, the single wire can expand to create an apex region spaced from the plane formed by the support structure 920. This expansion of the single wire forms the curved shape (e.g., a dome shape), which defines and encloses a cavity or volume 370 capable of receiving and containing a fluid. The inherent spring force and shape memory of the at least one deformable member 950 allows the self-expansion from a compressed configuration into this three-dimensional expanded configuration when the constraining forces are removed upon deployment from the delivery member 400 lumen.

In some embodiments, the at least one deformable member 950 includes at least a portion thereof which can be over molded with a biocompatible material 955 to increase surface area and/or reduce irritation. For example, the biocompatible material can include a biocompatible plastic or silicone.

In some embodiments, the spacer device 900 is set into the desired expanded configuration during the manufacturing process and then straightened into a wire that fits within the delivery member 400 for introduction into the eye.

In some embodiments, in the expanded configuration, the at least one deformable member 950 (or the single wire) forms a convoluted, wavy pattern—alternating between curved $a_{1 \ldots x}$ and relatively straight sections $b_{1 \ldots x}$. For example, a sinuous structure that provides a continuous, looping pathway, forming and defining the interior volume 370 of the device.

FIG. 8A illustrates spacer device 900 with a single straight section $b_{1 \ldots x}$. FIG. 9A to FIG. 9C illustrate a spacer device 900 with three straight sections $b_{1 \ldots x}$. FIG. 9D to FIG. 9E illustrate a variant spacer device 900 which includes five straight sections $b_{1 \ldots x}$. The reader will understand that another variant may include more or less of the straight sections $b_{1 \ldots x}$, for example.

Each straight section $b_{1 \ldots x}$ bends smoothly at regular intervals, creating a continuous, undulating structure that aligns along the central axis of the device 900. The at least one deformable member 950 forms arches that rise and fall, shaping the internal volume and maximizing the use of available space without requiring a solid enclosure. This configuration allows the device to enclose or support materials within the internal volume, while maintaining an open structure that minimizes weight and material usage. The wave-like bends and curves of the at least one deformable member 950 allows the transition to the expanded configuration with an outward expansion while maintaining structural integrity.

In some embodiments, the spacer device 900 can form a shape having a single arch, as shown in FIG. 8A, FIG. 8B, FIG. 9I, and FIG. 9M.

Alternatively, the spacer device 900 can form a shape having a plurality of arches, as shown in FIG. 9A to FIG. 9E, FIG. 9N to FIG. 9O. In a variant, the spacer device 900 can have juxtaposed sections forming a shape having a plurality of arches, such as two single arch-forming body juxtaposed to form a plurality of arches a non-limiting illustration of which is shown in FIG. 9P.

Figure 9F:
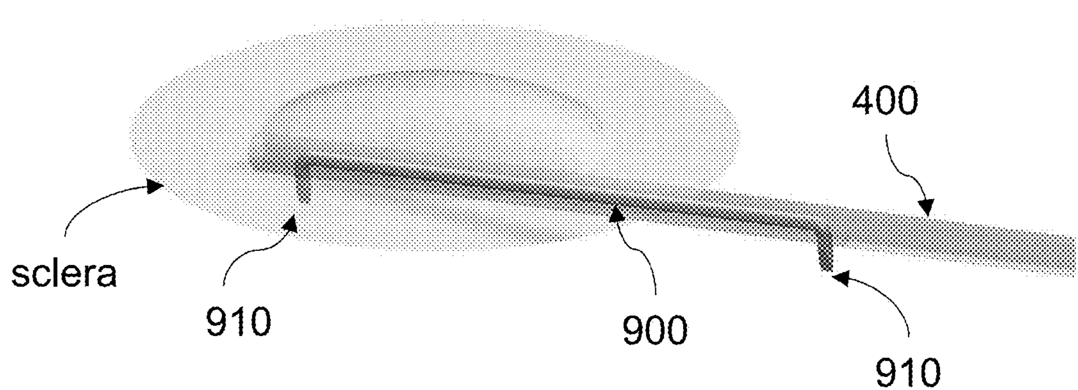
Figure 9G:
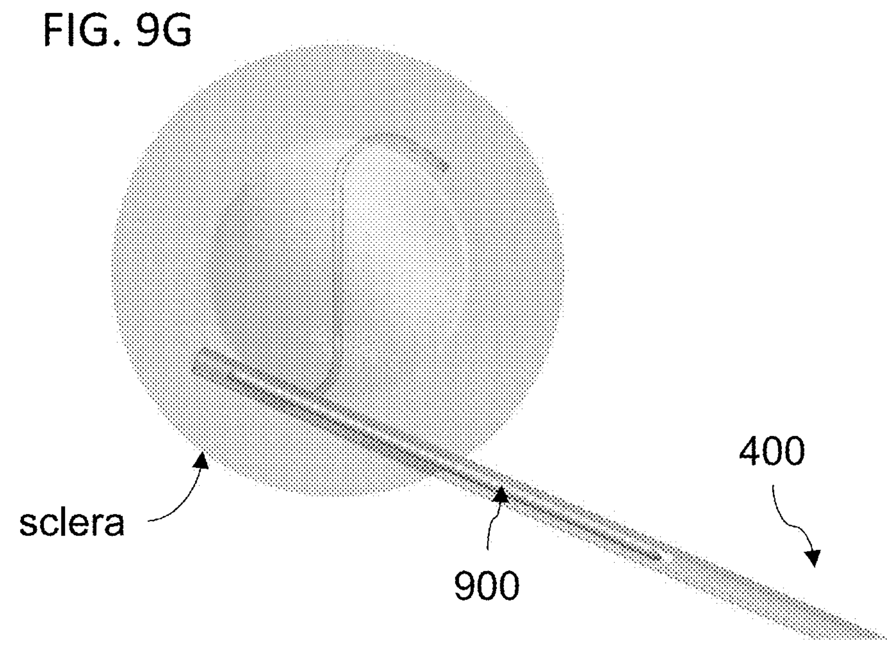
Figure 9L:
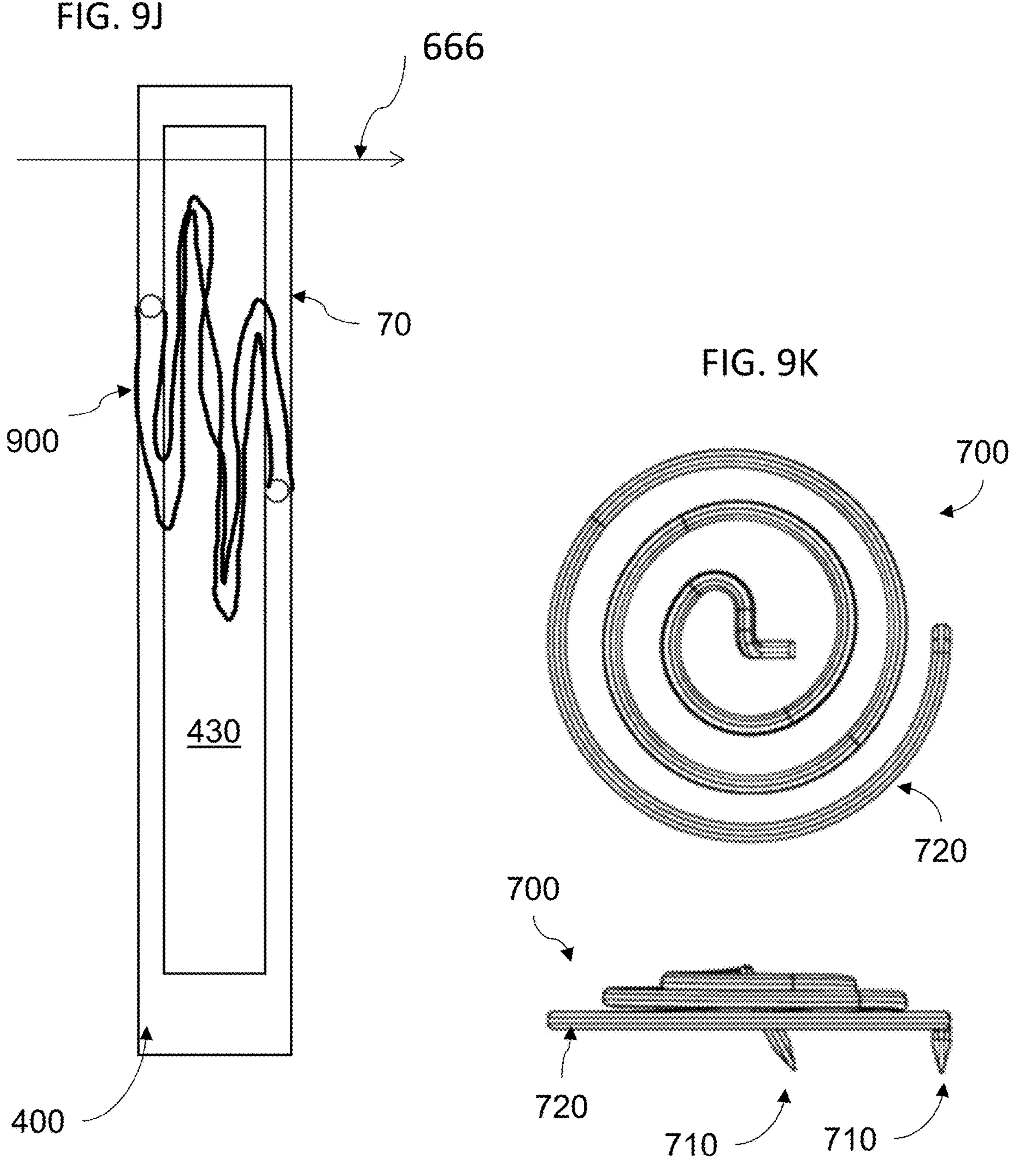
FIG. 9L is a side view of the spacer device of FIG. 9K.
Figure 9M:
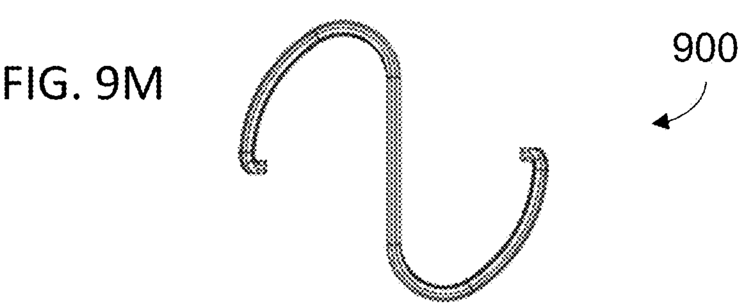
FIG. 9M to FIG. 9P are elevated views of the variants of the spacer device of FIG. 8A.
Figure 9N:
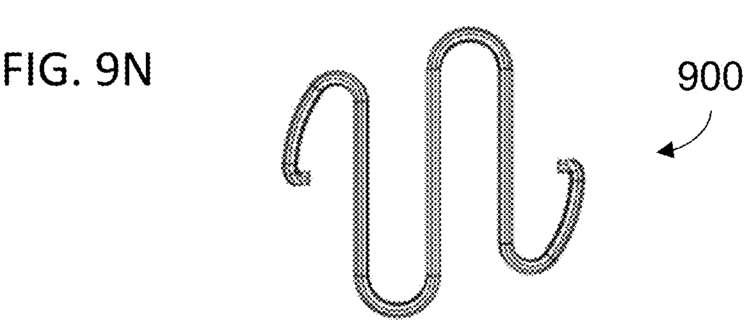
Figure 9O:
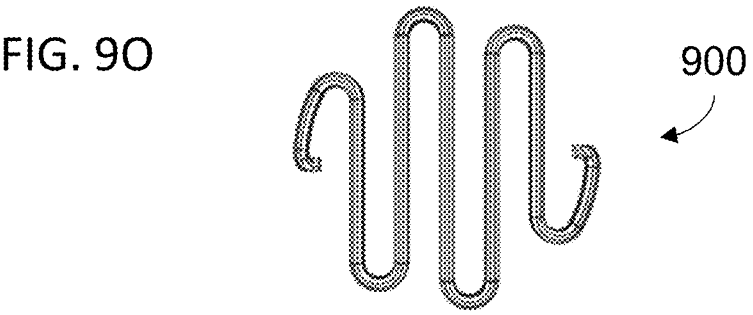
Figure 9P:
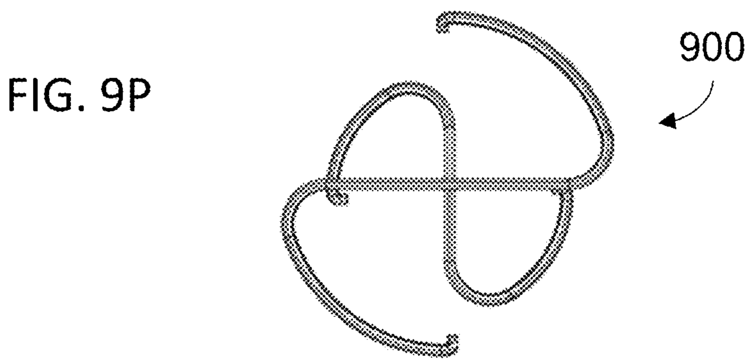

In some embodiments, when delivering the spacer device 900 into the eye, the user (e.g., surgeon) can position the delivery member 400 relatively perpendicular to the eye and feed a first end of the spacer device 900 wire into the surrounding eye tissue, anchoring the first end into the eye (e.g., with point sutures or by pressing an engaging element into eye tissue), as shown in FIG. 9F. The user then guides the rest of the straightened spacer device 900 wire through the entry point as shown in FIG. 9G, allowing the spacer device 900 wire to drop down and expand into the pre-formed expanded configuration shape, e.g., curved shape 990, which is shown in FIG. 9A to FIG. 9C as a virtual shape.

In some embodiments, upon deployment from the delivery member 400, the spacer device 900 transitions to the expanded configuration, thus defining and enclosing the three-dimensional volume, which creates a dedicated space for drainage, collection, or other fluid management functions. At this stage, the user (e.g., surgeon) can secure the second end of the spacer device 900 wire into the surrounding eye tissue to provide additional anchoring (e.g., with point sutures or by pressing an engaging element into eye tissue), as shown in FIG. 9H. This helps secure the device 900 in place and prevents migration or displacement over time.

In some embodiments, the spacer device 900 wire has a cross-section size, as well as forms a three-dimensional shape having a size, which may vary so long as the spacer device 900 wire has a diameter small enough to allow for minimally invasive insertion yet provides sufficient structural integrity to maintain the desired pre-formed expanded configuration shape. For example, the convoluted wire pattern can provide structural integrity to maintain the curved shape and interior volume, while also allowing the device 900 to conform to the patient's unique eye anatomy.

In some embodiments, delivery of the spacer device 900 is performed by sweeping laterally the delivery member housing the spacer device, as shown in FIG. 9J with arrow 666.

Compared to other fluid management approaches, this device design offers several advantages. Its shape-memory wire construction allows for a straightforward, single-step implantation process. The open, three-dimensional cavity also allows for greater fluid capacity and more efficient management compared to flat or single-channel drainage devices. The arrangement described herein is particularly suitable for applications where a lightweight but structurally stable framework is beneficial, such as in biomedical, filtration, or fluid transport systems.

Fourth Implementation

FIG. 10A to FIG. 10I illustrate a fourth non-limiting implementation of a spacer device that is arranged and configured in accordance with certain features, aspects, and advantages of the present disclosure. These figures show several variants of this spacer device implementation.

In some embodiments, the spacer device 800 can be configured to reversibly transition from a first, compressed configuration (having a lower profile) to a second, expanded configuration (having a larger profile). For example, the spacer device 800 can have self-expandable characteristics and is reversibly movable from the compressed configuration to the expanded configuration, and vice versa.

In some embodiments, the spacer device 800 is configured to reversibly transition between the compressed configuration, sized to fit within at least a portion of the delivery member 400, and the expanded configuration.

In some embodiments, the spacer device 800 comprises a flexible, generally contoured body shaped to conform to anatomical tissue surfaces, such as the sclera or sub-Tenon's space. In this context, the term "flexible" generally refers to the ability of the body to deform, bend, or compress to fit within a delivery cannula and expand to the initial shape upon exiting the delivery cannula.

In some implementations, the anterior-facing portion of the spacer device body includes a relief cut-out 870 (a recessed or scalloped geometry) designed to prevent direct contact with the cornea. This anterior relief 870 can serve a dual purpose: it can prevent irritation or abrasion of the corneal tissue and can also maintain a clear zone for optical coherence and implant alignment. The anterior relief 870 also supports the formation of an anterior bleb space, allowing fluid to accumulate while preserving corneal clearance.

Toward the posterior region of the spacer or along side walls, one or more enlarged posterior cut-outs or elevated walls 820 can be incorporated. These cut-outs or elevated walls 820 can promote posterior and/or lateral fluid migration, enabling the bleb to extend in a substantially posterior direction, away from the visual axis and sensitive anterior structures. This configuration can also ensure that the spacer device 800 supports both anterior bleb formation, for initial pressure reduction, and posterior bleb expansion, for long-term drainage and tissue accommodation.

The cut-outs or elevated walls 820 in the spacer device 800 can also serve an additional role in the device's mechanical flexibility and deliverability. Specifically, the cut-outs or elevated walls 820 can enable the spacer to be compressed, folded, or rolled longitudinally, allowing it to be inserted through the delivery member tapered portion during delivery. Once deployed, the spacer device 800 expands or unfolds into its expanded, operative configuration, where its inherent curvature and structural design restore the intended spacing and flow-directing geometry, as shown in FIG. 15A to FIG. 15D.

In some embodiments, the spacer device is intended to be positioned with its curved, anterior surface 870 oriented toward the limbus, and its posterior legs or extensions 880 guiding fluid posteriorly over and around an associated glaucoma channel, implant or shunt. This anatomical orientation advantageously ensures that the spacer device lifts the overlying conjunctiva to create and maintain the bleb space while also preserving the patency of the underlying drainage implant or sclerostomy. The posterior legs or extensions 880 may act as flow channels or struts to maintain space while also directing fluid expansion in the desired direction, as shown in FIG. 15A to FIG. 15D.

At least two size variants of the spacer device can be envisioned to accommodate anatomical differences across species and patients. A smaller version, scaled to accommodate a globe diameter of approximately 16 mm, is intended for preclinical testing in rabbit models. A larger variant, sized for approximately 25 mm globe diameters, is configured for use in human or porcine eyes. While both variants may retain one or more of the features described herein (engaging elements, central slots, posterior cut-outs, and compressibility for delivery) each may differ in curvature, length, and cut-out dimensions to optimize performance in their respective ocular environments.

The multi-path fluid outflow capability of the spacer device, combined with its anatomical curvature and delivery compatibility, makes it particularly suitable for minimally invasive ophthalmic surgeries where controlled bleb formation and implant clearance are advantageous. The integration of flow-directing structures and relief geometries ensures not only effective intraocular pressure reduction but also compatibility with a wide range of implant geometries and ocular anatomies.

In some embodiments, the spacer device 800 is composed of a medical grade material suitable for use in the eye. For example, the spacer device 800 can include a material allowing it to transition from the compressed configuration to the expanded configuration, with an amount of elasticity. For example, the spacer device 800 can be formed from any suitable material, including but not limited to metals, polymers, elastomers, hydrogels, smart materials, or composites thereof. For example, suitable metals include shape memory alloys such as Nitinol (nickel-titanium alloy), copper-aluminum-nickel alloys, and iron-based shape memory alloys. Suitable polymers include polyamide, polyimide, polyethylene terephthalate (PET), polytetrafluoroethylene (PTFE), polyetheretherketone (PEEK), polylactic acid (PLA), polycaprolactone (PCL), polyurethanes, polyhydroxybutyrate (PHB), chitosan, polydioxanone (PDO), silk fibroin, acrylic polymers, and thermoplastic or thermoset materials. For example, polyurethanes include thermoplastic polyurethane (TPU), medical-grade polyether urethane, and silicone-polyurethane copolymers. For example, acrylic polymers include hydrophobic acrylic, hydrophilic acrylic, and crosslinked copolymers of methacrylate and acrylate derivatives. Elastomeric materials may also be used, such as silicone-based elastomers. For example, silicone-based elastomers include polydimethylsiloxane (PDMS), crosslinked medical-grade silicone, and room temperature vulcanizing (RTV) silicone. Hydrogels may be used, including but not limited to poly (2-hydroxyethyl methacrylate) (PHEMA), polyacrylamide-based hydrogels, polyvinyl alcohol (PVA) hydrogel, collagen-hydrogel copolymers, and polyethylene glycol (PEG)-based hydrogels. Smart or stimuli-responsive polymers may also be used, including thermoresponsive and shape memory polymers. For example, thermoresponsive polymers include poly(N-isopropylacrylamide) (PNIPAM), poly(N-vinylcaprolactam) (PVCL), and poly(ethylene glycol)-based block copolymers. Biodegradable polymers with form retention properties may also be used. For example, such biodegradable polymers include poly(lactic-co-glycolic acid) (PLGA), polycaprolactone (PCL), polydioxanone (PDO), and poly(L-lactic acid) (PLLA). Other suitable materials may include magnesium alloys, Collamer (hydroxyethyl methacrylate with porcine collagen), polyHEMA-collagen copolymers, acrylic-urethane hybrids, or any biocompatible composite or combination thereof.

Compared to other fluid management approaches, this device design offers several advantages. Its shape-memory construction allows for a straightforward, single-step implantation process. The open, three-dimensional cavity also allows for greater fluid capacity and more efficient management compared to flat or single-channel drainage devices. The arrangement described herein is particularly suitable for applications where a lightweight but structurally stable framework is beneficial, such as in biomedical, filtration, or fluid transport systems.

Three-Dimensional Volume

In some embodiments, the spacer device described herein defines an internal three-dimensional volume 370, which has a suitable dimension to receive and manage fluids. For example, for the formation of a bleb for management of intraocular pressure. For example, in the case of spacer device 800, the three-dimensional volume 370 is defined within the walls of the surface 825.

In some embodiments, the spacer device described herein can have a height Y at the apex, a first diameter X and a second diameter Z (as shown in FIG. 3), which are suitable to form the internal three-dimensional volume 370 of desired dimension.

In some embodiments, the height Y at the apex may be of from about 0.5 mm to about 2.5 mm, including any ranges or values therein. For example, the height Y at the apex may be of about 0.5 mm, about 1.0 mm, about 1.5 mm, about 2.0 mm, or about 2.5 mm. Preferably, the height Y at the apex may be from about 1.2 mm to about 1.6 mm, including any ranges or values therein. More preferably, the height Y at the apex may be from about 1.3 mm to about 1.5 mm, including any ranges or values therein.

In some embodiments, the spacer device described herein can have a structure thickness of from about 0.4 mm to about 1.0 mm, including any ranges or values therein. For example, the structure thickness can be of about 0.4 mm, about 0.5 mm, about 0.6 mm, about 0.7 mm, about 0.8 mm, about 0.9 mm, or about 1.0 mm. Preferably, the structure thickness can be from about 0.6 mm to about 0.8 mm, including any ranges or values therein.

In some embodiments, the first diameter X and the second diameter Z may be independently selected from a size in the range of from about 2.5 mm to about 4.0 mm, including any ranges or values therein. For example, the first diameter X and the second diameter Z may be independently about 2.5 mm, about 3.0 mm, about 3.5 mm, or about 4.0 mm. Preferably, the first diameter X and the second diameter Z have an identical size. More preferably, the first diameter X and the second diameter Z have a size of about 3.5 mm.

In some embodiments, the three-dimensional volume 370 may have a height at the apex of from about 600 μm to about 900 μm, including any ranges or values therein. For example, a height of about 600 μm, about 700 μm, about 800 μm, or about 900 μm. Preferably, the cavity height is of about 750 μm.

In some embodiments, the aforementioned size values can be more suited for adult patients having an internal ocular pressure (IOP) of about 8 mmHg. For example, the size values may differ for adult patients having a different IOP or for pediatric patient, where a device having a larger width and smaller height may be desirable, in some cases even providing better results.

In some embodiments, the three-dimensional volume 370 is configured for receiving a fluid therein. For example, the spacer device described herein can be in fluid communication with the anterior chamber of the eye 20 through a channel generated through eye tissue layer such as with canaloplasty (a procedure to open the Schlemm's canal), through a Minimally Invasive Suction Trabeculotomy (MIST) (technique that involves using a specialized instrument to create a small opening in the trabecular meshwork, the eye's natural drainage pathway, to improve fluid outflow), or through an ocular implant 100, such as a shunt, disposed between the anterior chamber and the ocular tissue spacer. The channel, MIST opening, or ocular implant 100 can form a drainage channel and the spacer device described herein can thus operate as a structure that defines and contains a three-dimensional volume configured to receive aqueous humor flowing out of the anterior chamber of the eye and draining through the channel, MIST opening, or ocular implant, thus reducing eye internal pressure.

Figure 14:
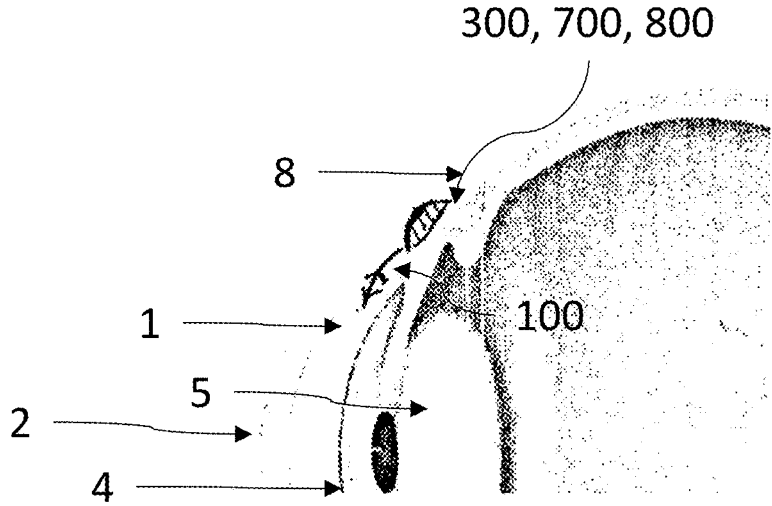
FIG. 14 is a cross-sectional diagram of the spacer device of the present disclosure in conjunction with a shunt placed in an eye, in accordance with non-limiting embodiments of the present disclosure.
Figures 15A, 15B:
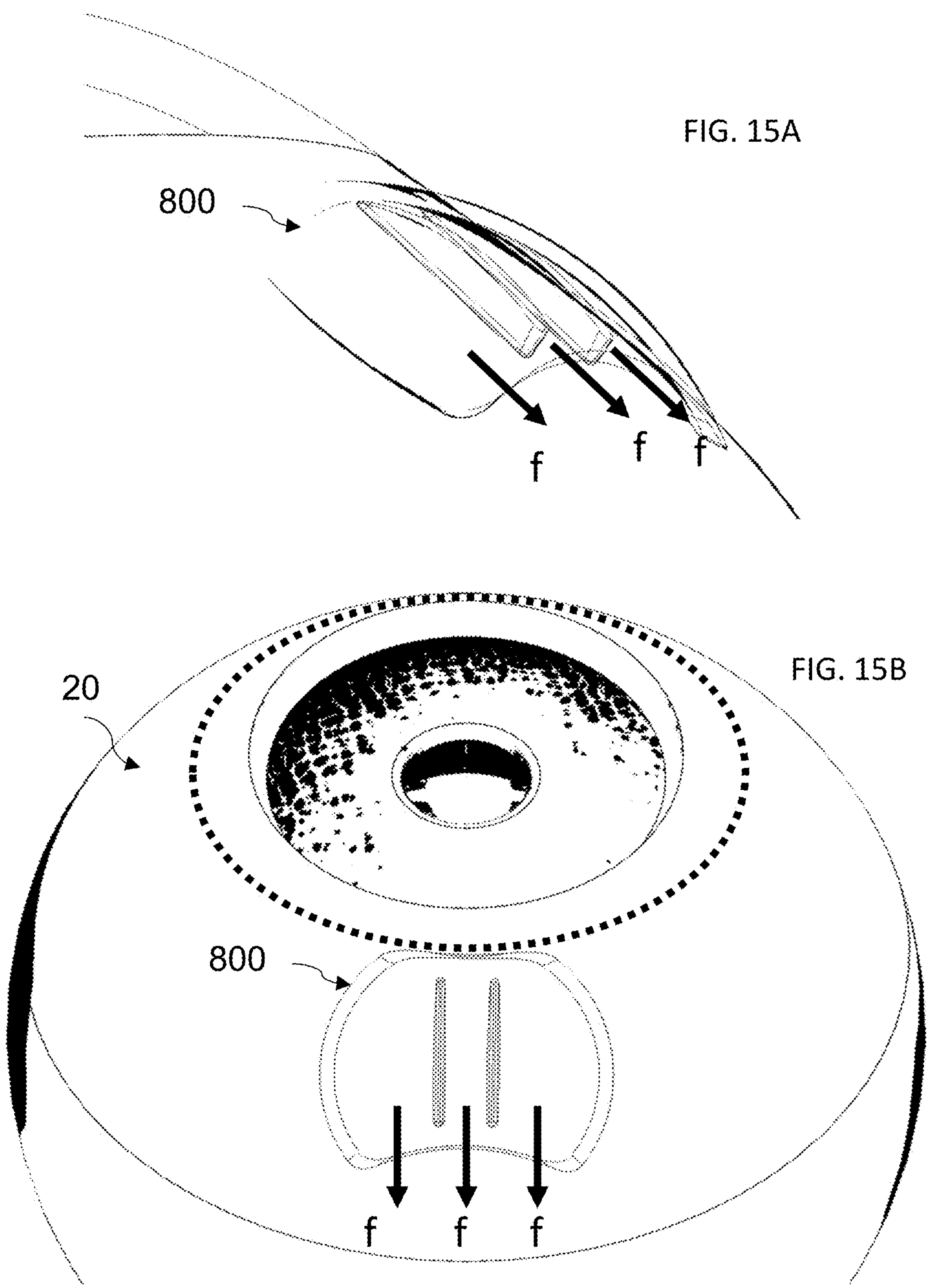
FIG. 15A to FIG. 15D are non-limiting illustrations of a spacer device implanted into an eye, in accordance with non-limiting embodiments of the present disclosure.
Figures 15C, 15D:
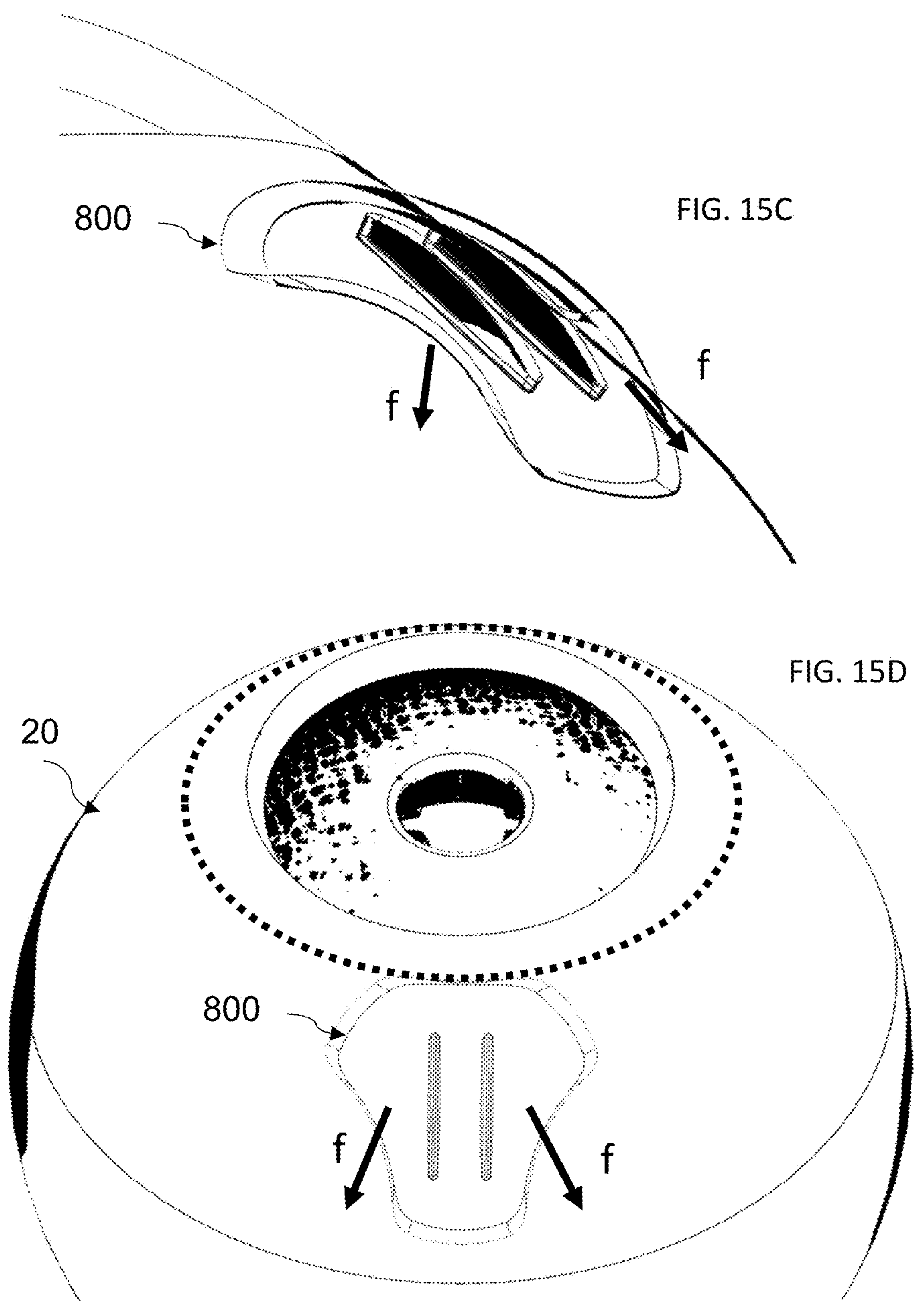

FIG. 14 illustrates the non-limiting case where the spacer device described herein is in fluid communication with the anterior chamber through ocular implant 100.

Securing Features

In some embodiments, the spacer device described herein further includes one or more securing features for securing the spacer device on an eye surface.

For example, the one or more securing features may include engaging elements 310, 710, 910 for mounting or securing the spacer device to an eye tissue. In another example, the one or more securing features may include apertures 915 for fixing through suture point, as shown in FIG. 8A.

In some embodiments, one or more engaging elements 310, 710 are disposed on the periphery of the support structure 320, 720. Each of the engaging elements 310, 710 extends away from the surface of the support structure 320, 720.

In some embodiments, one or more engaging elements 910 is disposed at an end of the support structure 920. The one or more engaging elements 910 extends in a direction substantially perpendicular to a plane formed by the support structure 920.

In some embodiments, the one or more engaging elements 310, 710, 910 is configured to anchor to an eye tissue structure. For example, when the spacer device described herein is properly positioned in the eye, the one or more engaging elements 310, 710, 910 engages with eye tissue structures to prevent movement of the spacer device relative to the eye, thus allowing proper functioning thereof.

Figure 10A:
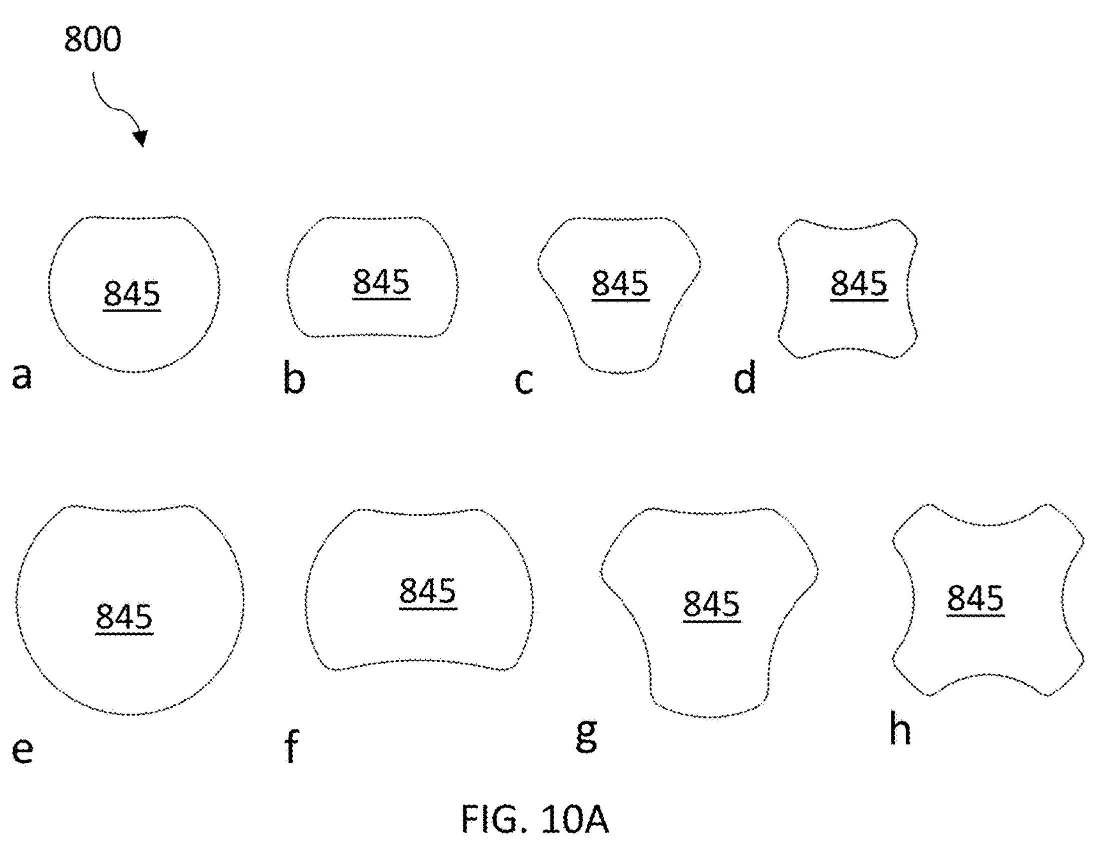
FIG. 10A is a non-limiting top elevated view of a fourth implementation of a spacer device for deployment within an eye, in an expanded configuration, as well as variants thereof in accordance with non-limiting embodiments of the present disclosure.
Figure 10B:
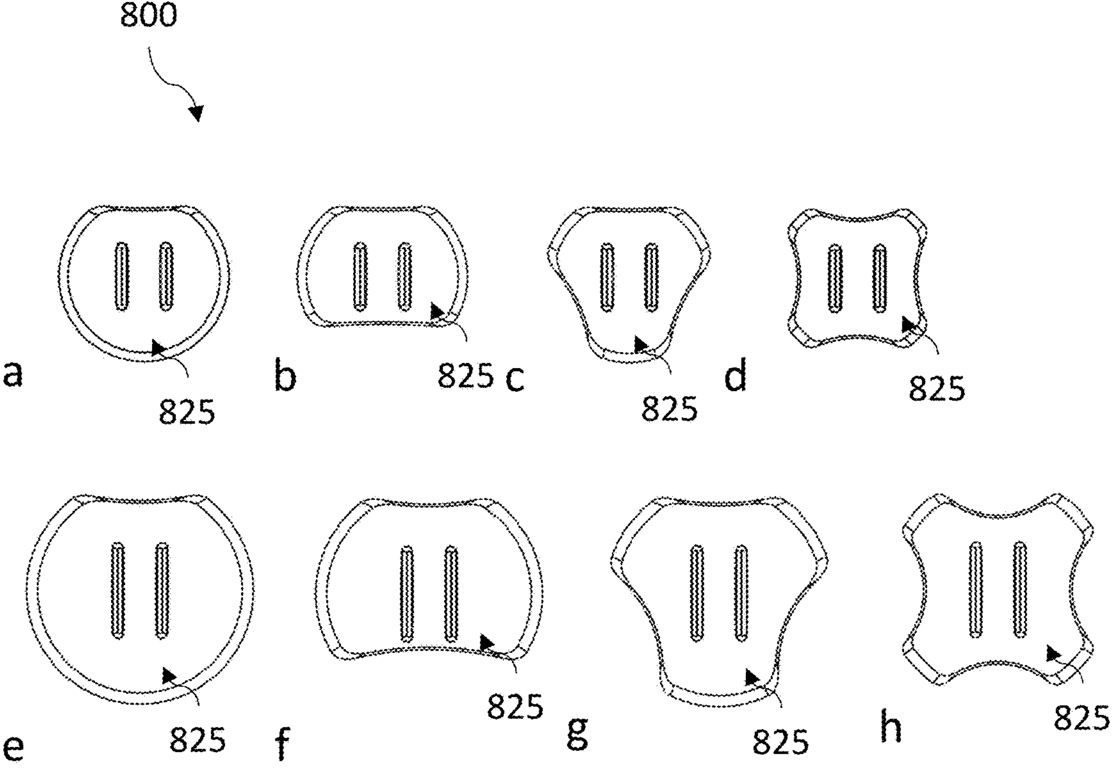
FIG. 10B is a non-limiting bottom view of the spacer device and variants thereof of FIG. 10A, in accordance with non-limiting embodiments of the present disclosure.
Figure 10C:
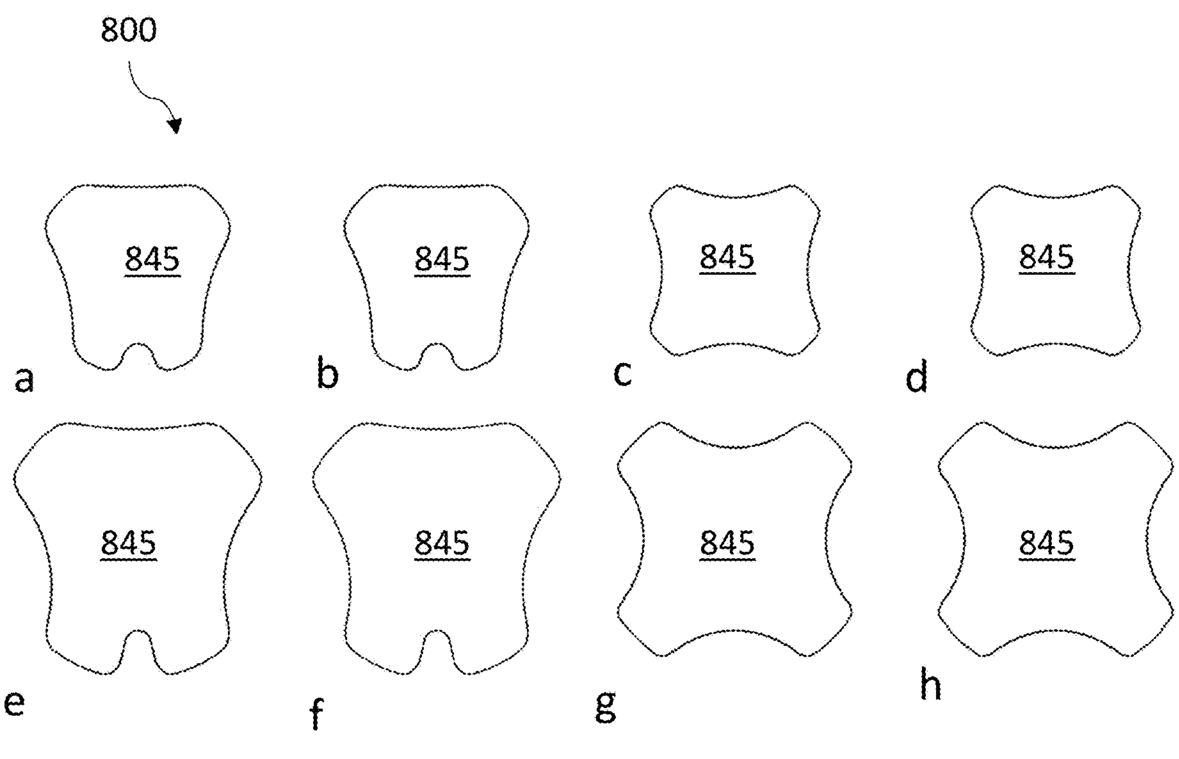
FIG. 10C is a non-limiting top elevated view of additional variants of the spacer device and variants of FIG. 10A, in accordance with non-limiting embodiments of the present disclosure.
Figure 10D:
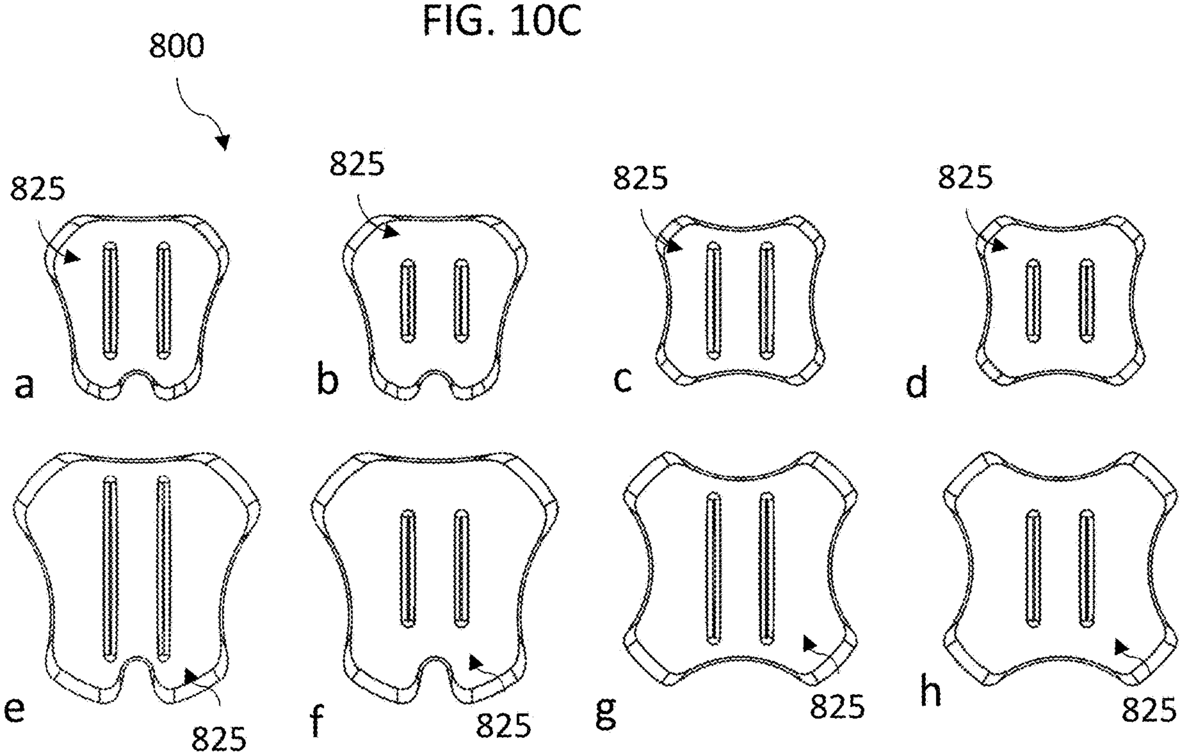
FIG. 10D is a non-limiting top bottom view of additional variants of the spacer device and variants of FIG. 10C, in accordance with non-limiting embodiments of the present disclosure.
Figure 10E:
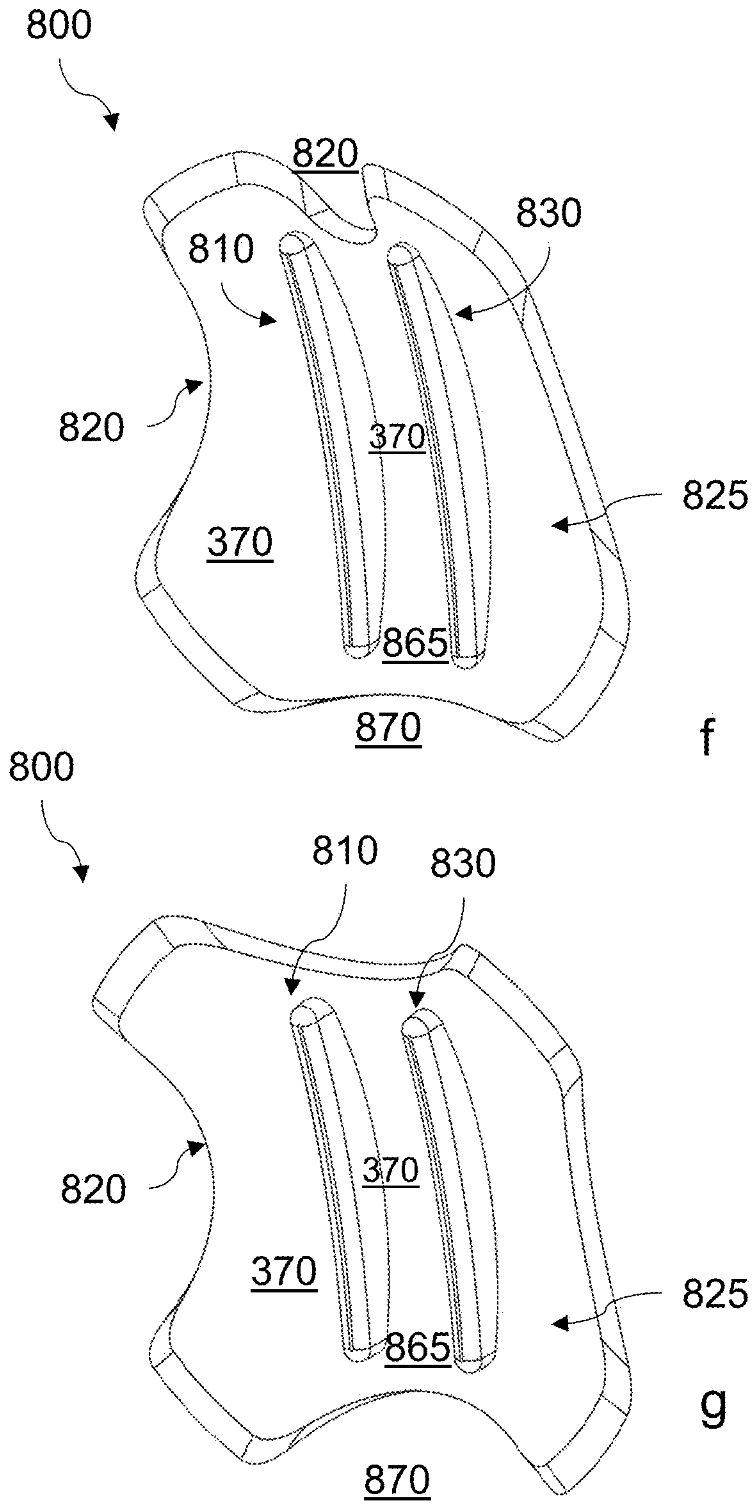
FIG. 10E is a non-limiting bottom perspective view of specific embodiments from FIG. 10D, in accordance with non-limiting embodiments of the present disclosure.
Figures 10F, 10G, 10H:
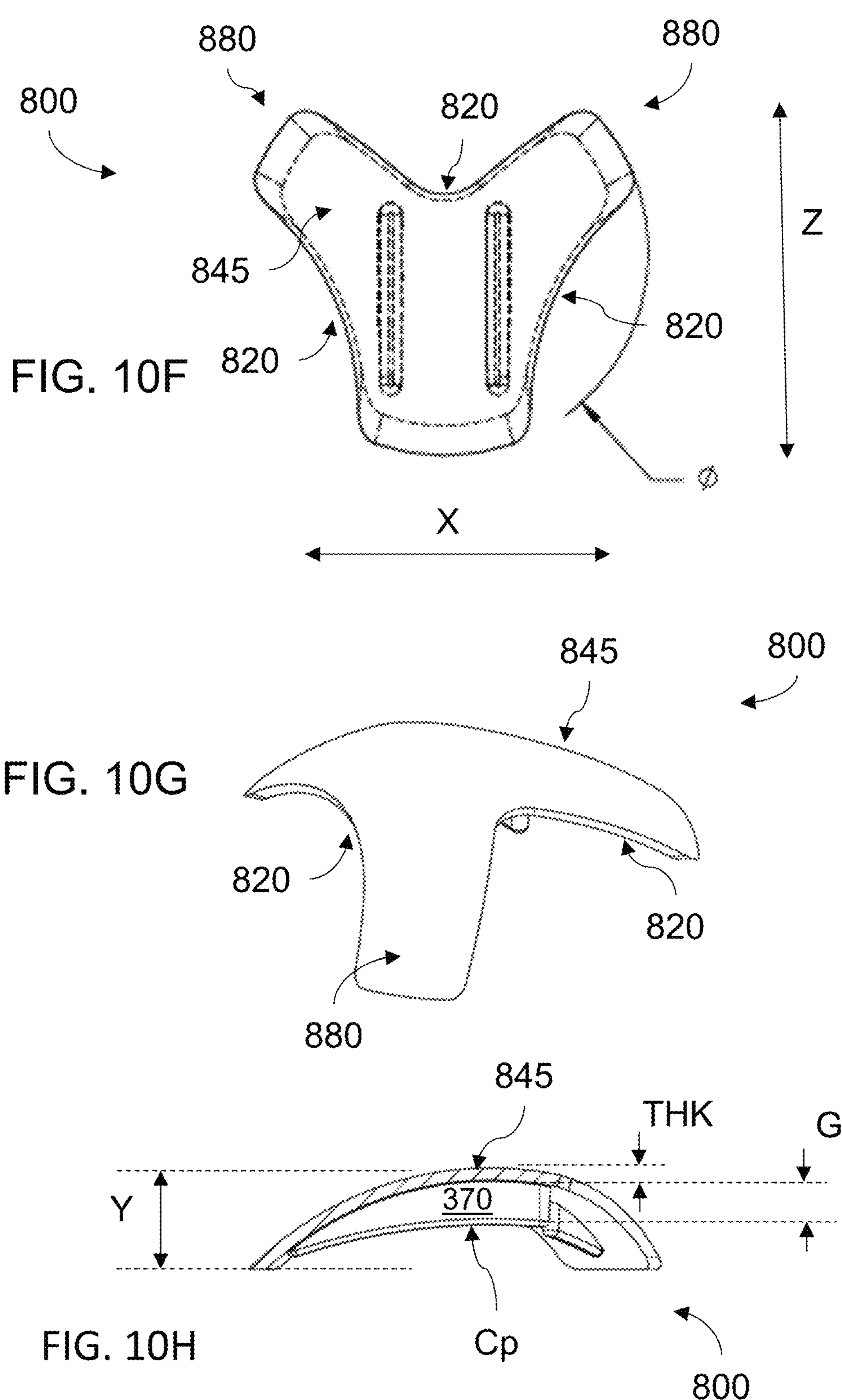
FIG. 10F is an elevated bottom view of another variant of the spacer device, in accordance with non-limiting embodiments of the present disclosure.
FIG. 10G is a side view of the spacer device of FIG. 10F.
FIG. 10H is a cross-side view of the spacer device of FIG. 10G.
Figure 10I:
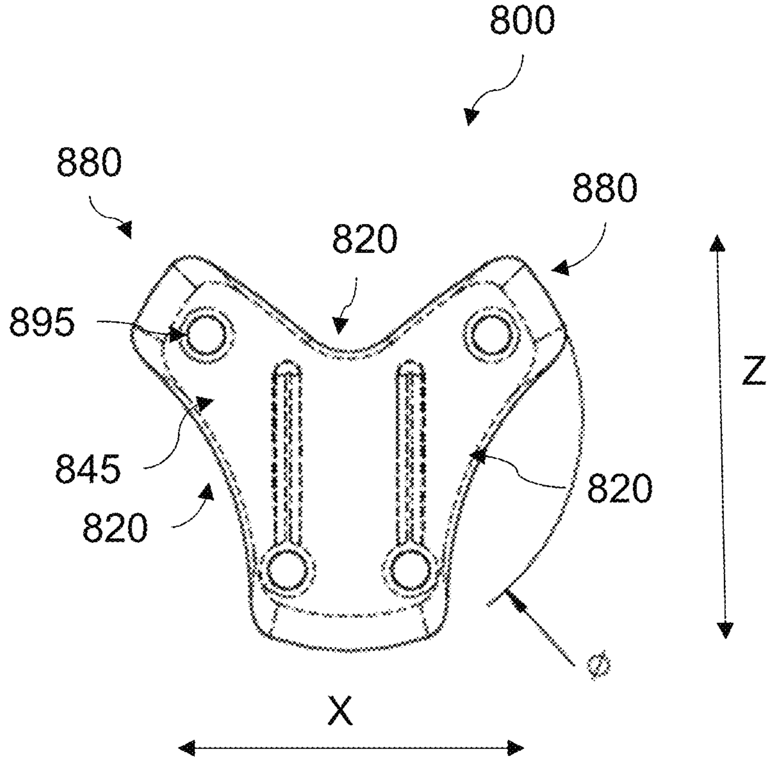
FIG. 10I is a variant of the spacer device of FIG. 10F.

In some embodiments, the spacer device 800 includes one or more centrally positioned elongate engaging elements 810, 830 extending along a longitudinal axis of the device. FIG. 10E shows a pair of engaging elements 810, 830. These engaging elements 810, 830 are configured to engage with a corresponding delivery mechanism, such as a delivery rod 550 (described elsewhere in this text) during the implantation procedure, and/or with an eye tissue surface. For example, the elements 810, 830 may define shallow grooves, channels, or slots adapted to receive prongs or fingers of the delivery rod 550, thereby ensuring secure retention and controlled release of the device as it is advanced through the delivery member. The engagement features may be integrally molded or formed as part of the spacer device 800 and may contribute to maintaining device orientation during deployment.

In some embodiments, the spacer device described herein can be configured to be positioned under the conjunctiva or the Tenon's capsule of the eye. The one or more engaging elements then engages with an eye tissue to prevent movement of the spacer device relative to the eye.

In some embodiments, the one or more engaging elements (such as 310, 710, and 910) can be hooks or anchors, which are configured to engage with eye tissue structures, such as the sclera.

Delivery Device

The spacer device described herein can be delivered and positioned in an eye with any suitable medical delivery device having suitable characteristics. For example, the medical delivery device may include a delivery member which is configured for housing the spacer device. For example, the medical delivery device may include a piercing tip on the delivery member configured for piercing an eye tissue layer, for delivery of the spacer device.

A non-limiting implementation of a medical delivery device will now be described with reference to FIG. 4, and FIG. 11A to FIG. 12C.

In some embodiments, the device 200 includes a body 210 for grasping. For example, the body extends along a longitudinal axis Ω.

Figure 11A:
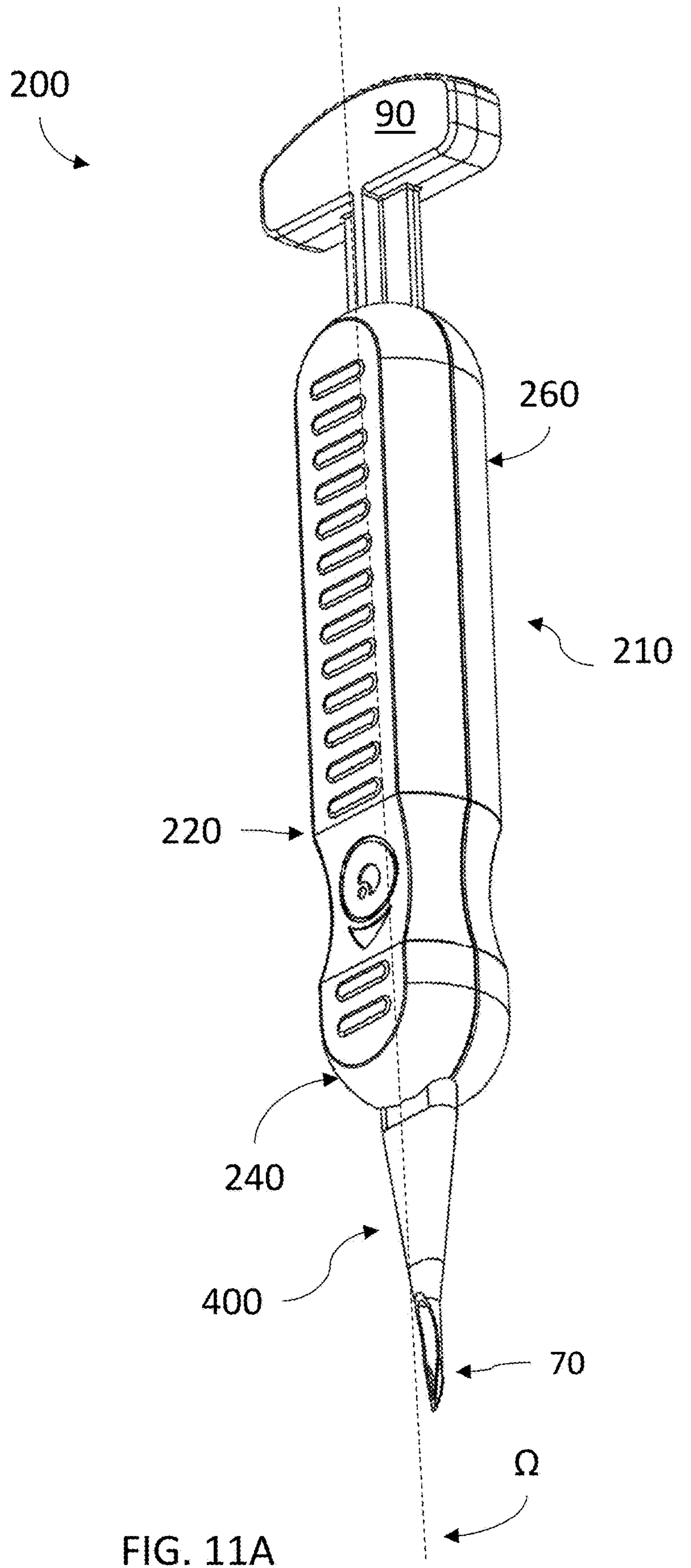
FIG. 11A, FIG. 11B, and FIG. 11D are non-limiting perspective views of a delivery device or components thereof for delivery of a spacer device as described herein on an eye, in accordance with non-limiting embodiments of the present disclosure.

While the specific embodiment shown in FIG. 11A is formed with a unitary single body, the reader will understand that in some variants, the device 200 may be formed of more than one segment, such as proximal and distal segments which can be coupled one to another through a suitable coupling joint, such as the device described in US 2025/0312194, the entire content of which is hereby incorporated by reference.

In some embodiments, the body 210 can be formed with first and second housing segments 240, 260. For example, the first and second housing segments 240, 260 may be configured for assembling one into another through any suitable coupling means. For example, the coupling means may include a plurality of screws, which are used to screw together the first and second housing segments 240, 260, thus forming the body 210. In other embodiments, the first housing segment 260 may include a plurality of peripherally spaced projections. Correspondingly, the second segment 260 may include a plurality of peripherally spaced notches that receive the corresponding projections to assemble the first and second housing segments 240, 260, thus forming the body 210.

In some embodiments, the body 210 may have at least a segment of the surface thereof, which is raised, depressed, grooved, or textured to improve hold by the user or to improve comfort of the user. The user may be a medical practitioner, such as an ophthalmologist, optometrist, eye surgeon, and the like.

In some embodiments, the body 210 is capable of being autoclaved or sterilized in some other manner. For example, the body 210 may be made from any suitable material, such as, but not limited to, polyethylene (PE) including low-density PE, high-density PE, or ultra-high molecular weight PE; polypropylene (PP); polytetrafluoroethylene; thermoplastic polyurethane; polycarbonate; polyphthalic acid; acrylic; acrylonitrile butadiene styrene (ABS); silicone, and the like.

In some embodiments, the body 210 may be configured to have a shape that facilitates handling of the device 200. For example, during use, the user may grip the device 200 with flexion of one or more fingers (e.g., with the middle finger) on a first side of the body 210 and with flexion and opposition of the thumb on a second side of the body 210, the first side being in opposite relationship to the second side.

In some embodiments, the body 210 may have suitable dimensions that facilitate handling of the device 200. For example, the body 210 may have a length of from about 50 mm to about 150 mm, including any values or ranges therein. For example, a length of about 55 mm, about 60 mm, about 65 mm, about 70 mm, about 75 mm, about 80 mm, about 85 mm, about 90 mm, about 95 mm, about 100 mm, about 110 mm, about 120 mm, about 130 mm, about 140 mm, or about 150 mm. For example, a length of about 74 mm. For example, the body 210 may have a height of about 10 mm to about 30 mm, including any values or ranges therein. For example, a height of about 10 mm, about 15 mm, about 20 mm, about 25 mm, about 30 mm. For example, a height of about 15 mm. For example, the body 210 may have a depth of from about 8 mm to about 20 mm, including any values or ranges therein. For example, a depth of about 8 mm, about 10 mm, about 12 mm, about 14 mm, about 16 mm, about 18 mm, or about 20 mm. For example, a depth of about 12.5 mm.

In some embodiments, the device 200 is a single use device which can be discarded after use.

Device 200 described herein includes components which can be adapted for specific ophthalmologic procedures. In some implementations, the device 200 may include other components that may benefit from the herein described features and advantages, which can be adapted for similar ophthalmologic procedures.

Delivery Member

In some embodiments, the device 200 described herein is equipped with a delivery member, which can be particularly useful to pierce an eye tissue layer.

In a non-limiting practical implementation, the device 200 includes delivery member 400. The delivery member 400 can have a proximal portion 450 which couples with a distal end of the device body 210 and can have a distal portion 455.

The delivery member 400 defines an internal cavity or lumen 420 extending from a distal end to a proximal end thereof.

In some embodiments, the delivery member 400 comprises a piercing tip 70 at the distal end thereof.

Figure 11B:
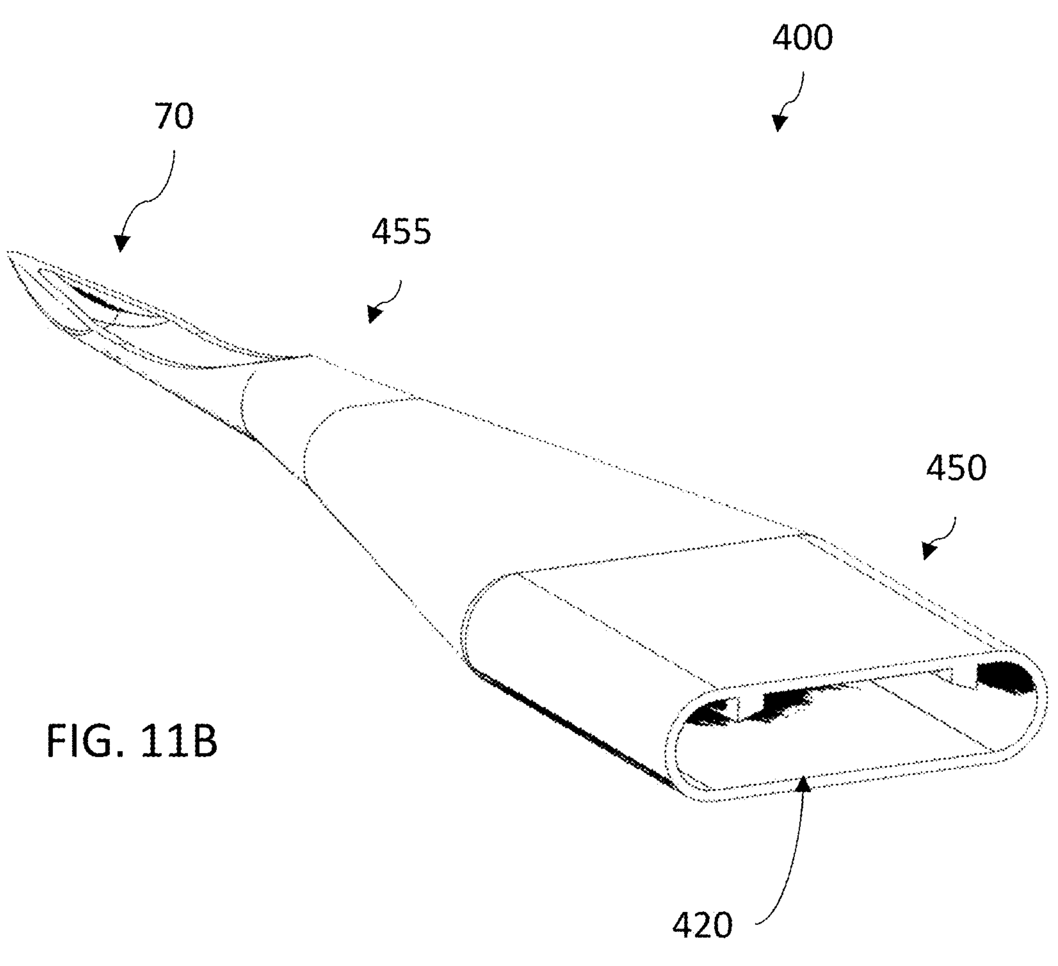
Figure 11D:
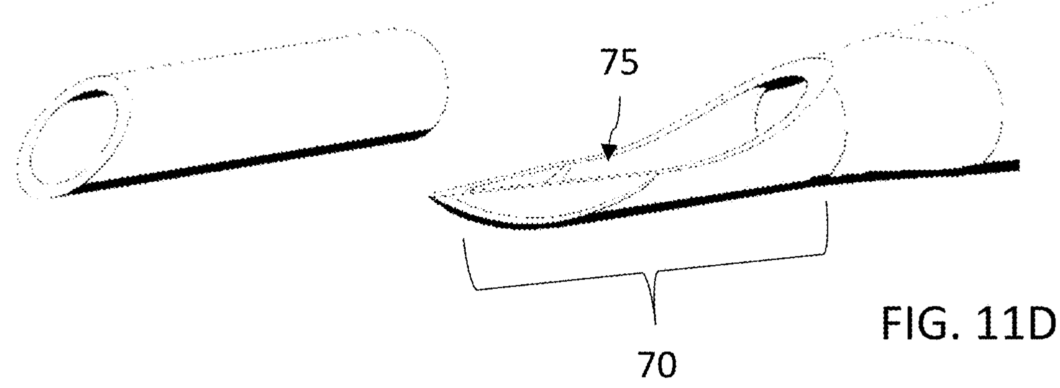

In some embodiments, the piercing tip 70 features a tapered, contoured cross-section 75 as shown in FIG. 11D, which significantly reduces the cross-sectional area of the distal end of the delivery member compared to conventional prior art designs. In contrast, prior art needle tips, such as that depicted in FIG. 11C, typically employ a blunt or beveled cylindrical structure with an outer diameter (OD) of approximately 1.7 mm to accommodate implant insertion. This standard geometry necessitates creating a relatively large entry wound in the eye tissue (e.g., conjunctiva), potentially increasing tissue trauma and affecting healing outcomes. In contrast, the piercing tip 70 provides a low-profile needle tip in which the cross-sectional geometry at the distal end is reduced by more than about 50% relative to the conventional cylindrical prior art design. This is achieved through a tapered, crescent-shaped or scoop-like structure 75 that gradually narrows the lumen and external profile, while still allowing for delivery of the implant device through the internal lumen. The result is a minimized insertion profile, reducing the size of the eye tissue entry point required for implantation, thereby improving patient comfort and accelerating tissue recovery. This design also facilitates smoother tissue displacement and reduces insertion force, offering significant advantages in surgical handling and clinical outcomes for implant delivery.

In use, the piercing tip 70 can be positioned with the open cavity facing towards the eye surface as shown in FIG. 16B.

In some embodiments, proximal to the distal portion 455, the delivery member 400 can form an optional bend 420. This bend can be between about 10 and about 45 degrees. In a preferred embodiment, the bend is about 15 degrees. The eye has a curvature, and the bend 420 may conform to this curvature, as shown in FIG. 16B.

As illustrated in FIGS. 16A and 16B, the bend 420 can be a smooth, pre-formed angular deviation of the delivery member 400 from its primary longitudinal axis. In certain embodiments, the bend 420 is disposed at a location spaced proximally from the piercing tip 70 by a distance sufficient to preserve the tapered, contoured cross-section at the very distal end while reorienting the shaft segment immediately proximal thereto. The bend 420 can be configured with a defined bend angle within the range described above and a controlled bend radius to avoid kinking and lumen collapse, thereby maintaining patency of the lumen 420 for implant passage. The bend 420 is oriented such that, when the device 200 is approached from the superior quadrant of the eye, the distal portion 455 aligns tangentially to the curvature of the ocular surface and directs the piercing tip 70 toward the intended tissue plane (e.g., conjunctiva and underlying sclera) with an optimized approach vector.

The bend 420 can facilitate introduction of the delivery member 400 into the eye by accommodating the anatomical constraints associated with superior access, including the curvature of the globe, the presence of the superior eyelid and brow, and the spatial relationship of periocular structures. By offsetting the distal portion 455 relative to the proximal portion 450, the user (e.g., surgeon) can maintain a comfortable hand posture and instrument clearance while achieving a trajectory that reduces the risk of unintended corneal contact, minimizes impingement by the eyelid margin, and improves visualization of the entry site. The controlled angular orientation provided by the bend 420 thereby lowers insertion force and enhances controllability during initial piercing and advancement, contributing to safer tissue engagement and reduced trauma.

From a mechanical standpoint, the bend 420 may be formed with a curvature sufficient to preserve column strength and torsional responsiveness of the delivery member 400. In certain embodiments, the bend 420 is engineered to distribute bending stresses over a finite bend radius, reducing local strain concentrations and mitigating the risk of work hardening or crack initiation in metallic shafts, or buckling in polymeric shafts. The geometry of the bend 420 can be selected to maintain coaxial alignment of the lumen 420 and minimize internal flow disruption, thereby allowing smooth passage of the implant. Suitable materials for the delivery member 400 can be processed (e.g., through mandrel forming, heat setting, or thermoforming) to achieve the desired bend angle and radius without compromising lumen integrity.

Compared to embodiments without the bend 420, the superior-approach configuration depicted in FIGS. 16A and 16B offers improved ergonomics, enhanced safety margins, and more predictable instrument trajectory. Devices lacking the bend may require steeper approach angles relative to the ocular surface, increasing insertion force, enlarging the entry wound, and raising the potential for slippage or off-axis piercing. In contrast, the bent configuration enables a lower-profile approach, improved tactile feedback, and better alignment with the ocular curvature, thereby reducing tissue trauma, improving wound apposition, and potentially accelerating healing.

In certain embodiments, the bend 420 may be indexed relative to the device body 210 so that rotational orientation is controlled; for example, a keyed interface at the proximal portion 450 can ensure that the angular offset is consistently aligned with the superior quadrant during use. The combination of the bend 420 with the tapered, contoured cross-section of the piercing tip 70 provides a technical effect in that the reduced distal profile eases tissue entry while the bend optimizes approach angle and instrument clearance, together enabling precise, low-trauma delivery of the device through the lumen 420.

In some embodiments, the delivery member 400 can have a suitable size, which may be selected from any one of the needle gauge size listed in Table 1:

TABLE 1

| Needle gauge | Outer diameter (inches) | Outer diameter (mm) | Inner diameter (inches) | Inner diameter (mm) |
|---|---|---|---|---|
| 7 | 0.180 | 4.572 | 0.150 | 3.810 |
| 8 | 0.165 | 4.191 | 0.135 | 3.429 |
| 9 | 0.148 | 3.759 | 0.118 | 2.997 |
| 10 | 0.134 | 3.404 | 0.106 | 2.692 |
| 11 | 0.120 | 3.048 | 0.094 | 2.388 |
| 12 | 0.109 | 2.769 | 0.085 | 2.159 |
| 13 | 0.095 | 2.413 | 0.071 | 1.803 |
| 14 | 0.083 | 2.108 | 0.063 | 1.600 |
| 15 | 0.072 | 1.829 | 0.054 | 1.372 |
| 16 | 0.065 | 1.651 | 0.047 | 1.194 |
| 17 | 0.058 | 1.473 | 0.042 | 1.067 |
| 18 | 0.050 | 1.270 | 0.033 | 0.838 |
| 19 | 0.042 | 1.067 | 0.027 | 0.686 |
| 20 | 0.03575 | 0.9081 | 0.02375 | 0.603 |
| 21 | 0.03225 | 0.8192 | 0.02025 | 0.514 |
| 22 | 0.02825 | 0.7176 | 0.01625 | 0.413 |
| 22s | 0.02825 | 0.7176 | 0.006 | 0.152 |
| 23 | 0.02525 | 0.6414 | 0.01325 | 0.337 |
| 24 | 0.02225 | 0.5652 | 0.01225 | 0.311 |
| 25 | 0.02025 | 0.5144 | 0.01025 | 0.260 |
| 26 | 0.01825 | 0.4636 | 0.01025 | 0.260 |
| 26s | 0.01865 | 0.4737 | 0.005 | 0.127 |
| 27 | 0.01625 | 0.4128 | 0.00825 | 0.210 |
| 28 | 0.01425 | 0.3620 | 0.00725 | 0.184 |
| 29 | 0.01325 | 0.3366 | 0.00725 | 0.184 |
| 30 | 0.01225 | 0.3112 | 0.00625 | 0.159 |
| 31 | 0.01025 | 0.2604 | 0.00525 | 0.133 |

In some embodiments, the piercing tip 70 may be of any gauge suitable for piercing the eye to cause an incision with a corresponding size sufficient to fit the spacer device described herein there through.

In some embodiments, the delivery member 400 may have at least a portion of a surface thereof which can be transparent, allowing pre-surgical visualization of the spacer device contained within lumen 420.

In some embodiments, the delivery member 400 houses the spacer device in the lumen thereof.

In some embodiments, the lumen portion of the proximal portion 450 houses the spacer device. For example, the lumen portion of the proximal portion 450 can house the spacer device in the expanded configuration, as shown in FIG. 12A.

In some embodiments, the delivery member 400 can have a generally rectangular or obround cross-section (e.g., elongated with curved shorter sides) at the proximal portion 450 and a generally tapered cross-section at the distal portion 455, as shown in FIG. 11B. In such embodiments, the spacer device transitions from the expanded configuration to the compressed configuration while traveling from the proximal portion 450 through the distal, tapered portion 455, as shown in FIG. 12B.

In some embodiments, the overall geometry of the delivery member 400 is streamlined to promote controlled tissue penetration. For example, in the embodiment where there is a transition from the wider proximal body to the narrower distal tip creates a low-profile, aerodynamic configuration. The body surface may exhibit smooth contours and continuous curvature, which minimizes sharp corners and promoting atraumatic interaction with surrounding tissue.

In some embodiments, the lumen 420 of the delivery member 400 matches the external shape and is configured to securely retain the spacer device in its delivery state. The delivery member 400 may include one or more internal structural features, such as guide rails, ledges, or retaining elements, to position the implant within the lumen and prevent premature deployment.

The delivery member 400 may include biocompatible plastic, polymer, or metal, such as stainless steel or a shape-memory alloy, and may be manufactured using machining, laser cutting, or electropolishing techniques to achieve the precision taper and sharpness required for ophthalmic procedures.

In use, the delivery member 400 can serve a dual function, namely piercing an ocular tissue layer, such as the sclera or conjunctiva, and containing and delivering the spacer device described herein. Upon reaching the target site within the eye, the medical delivery device may be actuated to reversibly transition the spacer device from the compressed configuration to the expanded configuration, and vice versa.

A particular delivery of the spacer device will be described with reference to FIG. 12A to FIG. 12C.

Figure 12C:
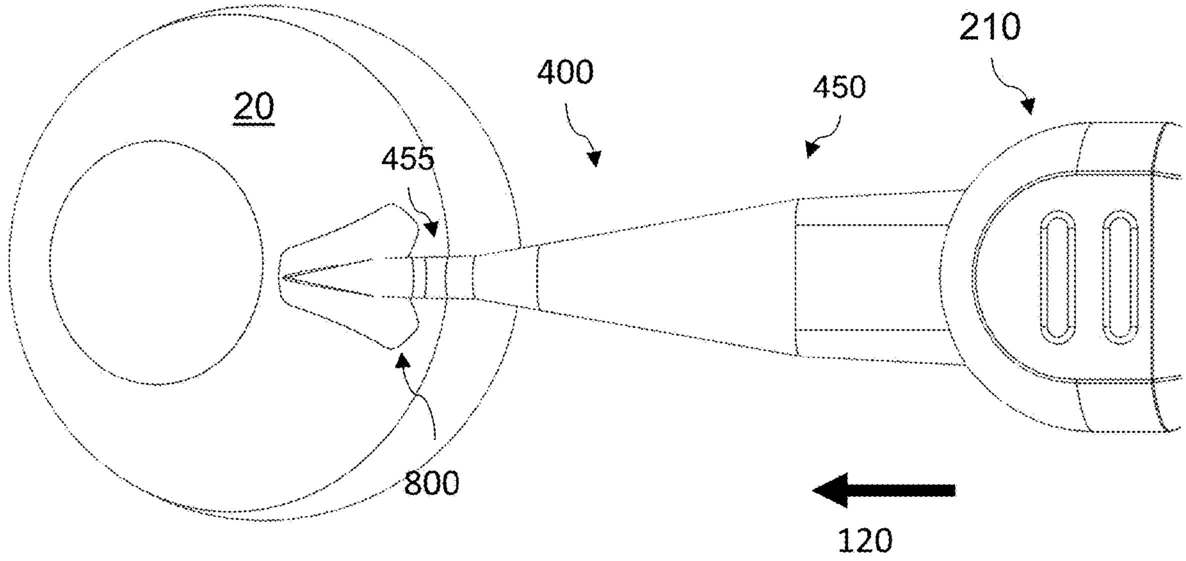

The delivery member 400 can house the spacer device described herein in an expanded configuration within lumen 420, as shown in FIG. 12A. Upon actuation of the delivery mechanism, including delivery rod 550, the spacer device 800 is displaced through the tapered portion of the delivery member with a coaxial anterior movement of the delivery mechanism shown with arrow 120 in FIG. 12B. At this point, the spacer device is compressed against the internal walls of the tapered portion of the delivery member 400, causing the spacer device 800 to compress or fold along its longitudinal axis into the compressed configuration. Upon continuing actuation of the delivery mechanism, the spacer device coaxially displaces through the lumen 430 out the distal tip 70, causing the spacer device to expand back into the expanded configuration, as shown in FIG. 12C.

In some embodiments, this reversible transitions to the expanded configuration occurs passively due to the material from which is composed the spacer device, as is discussed elsewhere in this text.

Actuator Assembly

In a non-limiting practical implementation, the device 200 further includes an actuator assembly configured to cause axial displacement movement of the spacer device. For example, the actuator assembly may include any suitable component or combination of components capable of providing the functionality described herein. While the following text describes particular implementations of an actuator assembly with reference to the figures, the reader will nevertheless understand that variations may be used to achieve a similar result.

FIG. 11A illustrates a non-limiting practical implementation of the actuation assembly, which includes suitable component or combination of components capable of providing the functionality described herein. For example, the actuation assembly includes a control point which can be engaged by the user to cause axial displacement movement of the spacer device.

In some embodiment, the control point can be a manually operated, $CO_2$-actuated, or screw-driven actuator. In some embodiment, the control point can take the form of a manually operated actuator 90. For example, the actuator 90 can be conveniently located on a proximal portion of the body 210 for ease of access with a finger, preferably the index.

In some embodiments, the actuator 90 may be a slider, trigger, wheel, or any other form that can be easily actuated, preferably with only one finger, such as the index.

In some embodiments, the actuator 90 may include teeth, or some other form that can provide friction, such as along an edge thereof to improve the user's ability to confidently contact, actuate (e.g., push), and release the actuator 90 even when moisture is present or when the user is wearing gloves. Furthermore, to improve the safety of using the device 200, the actuator 90 may include a locking mechanism or a means of preventing the unintended activation or release of said actuator.

In some embodiments, the control point can actuate and control a delivery mechanism to drive the spacer device through the lumen of the delivery member and eject the spacer device out the distal tip. In some embodiment, the delivery mechanism can include a delivery rod 550 where at least a portion thereof extends within the lumen 430. The delivery rod 550 functionally couples with the control point (e.g., actuator 90) and operates to push the spacer device described herein through the lumen 420 and out the distal tip 70. The delivery rod 550 can be operatively coupled to the control point (e.g., actuator 90) through one or more internal elements associated with the delivery device (not shown), such as those described in PCT/CA2023/051644, which is hereby incorporated by reference in its entirety.

For example, the delivery rod 550 may simply push out the spacer device when the delivery member 400 reaches the desired implantation site in the eye 20. Alternatively, the delivery rod 550 may releasably engage with the spacer device, such that when the spacer device reaches the desired site, the user releases the spacer device through engagement of a suitable actuator.

Figures 13A, 13B:
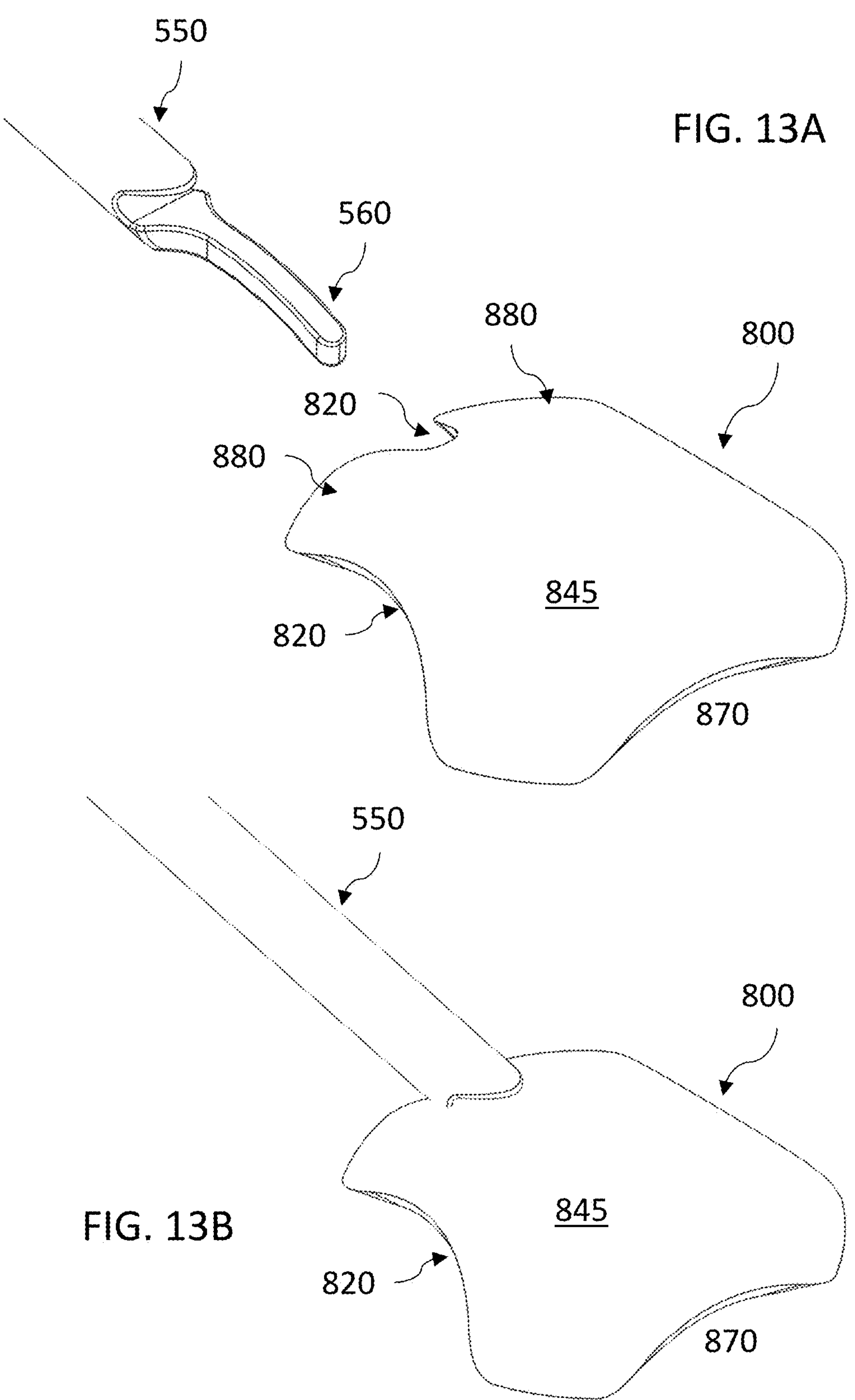
FIG. 13A and FIG. 13B are non-limiting top perspective views of a delivery stem engaging with the spacer device of FIG. 10F, in accordance with non-limiting embodiments of the present disclosure.

As shown in FIG. 13A, the distal end of the rod 550 may includes an engaging element 560 designed to engage with the spacer device. As discussed previously, in the case of spacer device 800, this spacer device may include one or more engaging elements 810, 830 configured to interact with at least the engaging element 560 in a manner that allows interfacing with the spacer device to stabilize the spacer device during insertion into a target anatomical site of a patient eye. For example, the engaging element 560 may comprise a flexible arm, spring-biased clip, or a molded protrusion with geometry tailored to interface with the spacer device body. The orientation shown in FIG. 13A illustrates the approach of rod 550 toward the spacer device 800 (variant g) in preparation for engagement.

In FIG. 13B, the retention element 560 is shown fully engaged with the spacer device 800. The coupling is designed to withstand forces encountered during insertion and navigation through tissue while ensuring accurate alignment of the spacer device with respect to the distal end of the rod 550. The engagement may be achieved via mechanical interference, frictional fit, or elastic deformation of one or more components. In some embodiments, the interface may also provide tactile or audible feedback to confirm proper seating of the components.

Figure 13C:
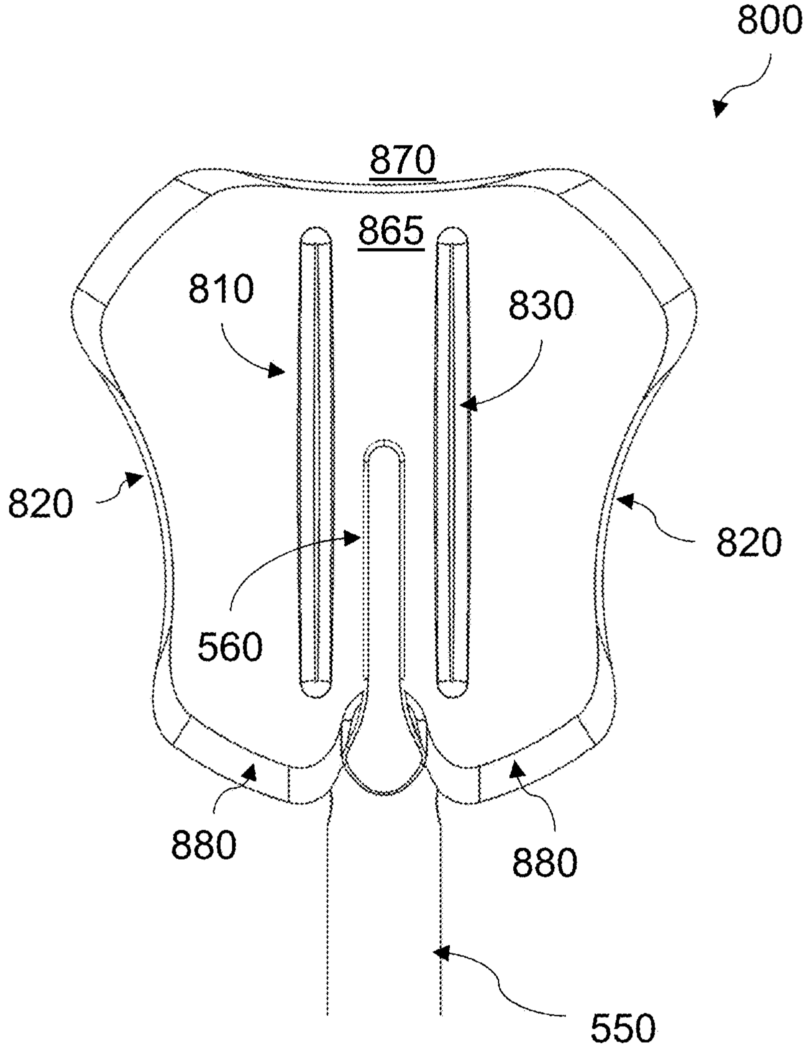
FIG. 13C is a non-limiting bottom elevated view of the delivery stem and the spacer device of FIG. 13B, in accordance with non-limiting embodiments of the present disclosure.

FIG. 13C presents a bottom elevated view of the system, illustrating in greater detail the internal configuration of the spacer device 800 and the spatial relationship between the engaging structures. The spacer device includes engaging elements 810 and 830 positioned on an internal surface 825, which is opposite an external surface 845, as shown in FIG. 10A to FIG. 10D.

In some embodiments, the engaging elements 810 and 830 are configured to receive and interface with at least portions of the engaging element 560 of the rod 550. These engaging elements 810 and 830 may include ribs, detents, or surface textures that enhance interface via increased surface contact or mechanical interlocking. In this configuration, the engaging element 560 is insertable into the central slot of the spacer device 800 such that it is flanked by the engaging elements 810 and 830. The geometry of the slots and the engaging element 560 is such that a releasable compression or snap-fit engagement can be achieved, providing reliable and repeatable attachment.

As shown, the spacer device 800 includes at least one central slot 865 positioned in between engaging elements 810 and 830. This slot 865 can form a primary conduit or fluid outflow path through the body of the spacer device 800. In use, aqueous humor exiting the anterior chamber via an ostomy or implant (e.g., glaucoma shunt) can pass through this central slot 865 and into the surrounding subconjunctival or episcleral space, thereby promoting bleb formation and fluid dispersion away from the limbus.

In alternate configurations, the body of the spacer device 800 may include elevated lateral sidewalls along its curved anterior-posterior profile. These elevated edges create lateral fluid escape channels, such that aqueous humor may exit not only through the central slot but also through the sides of the spacer device 800. These side channels help direct the flow of fluid posteriorly and laterally, facilitating more even distribution and expansion of the subconjunctival bleb, while also reducing anterior pressure and mechanical impingement near the corneal limbus.

The design may also allow for controlled release of the spacer device upon application of axial force, rotation, or actuation of a release mechanism (not shown). The ability to retain and then selectively release the spacer device is advantageous in clinical settings where repositioning or retrieval may be necessary.

Figure 13D:
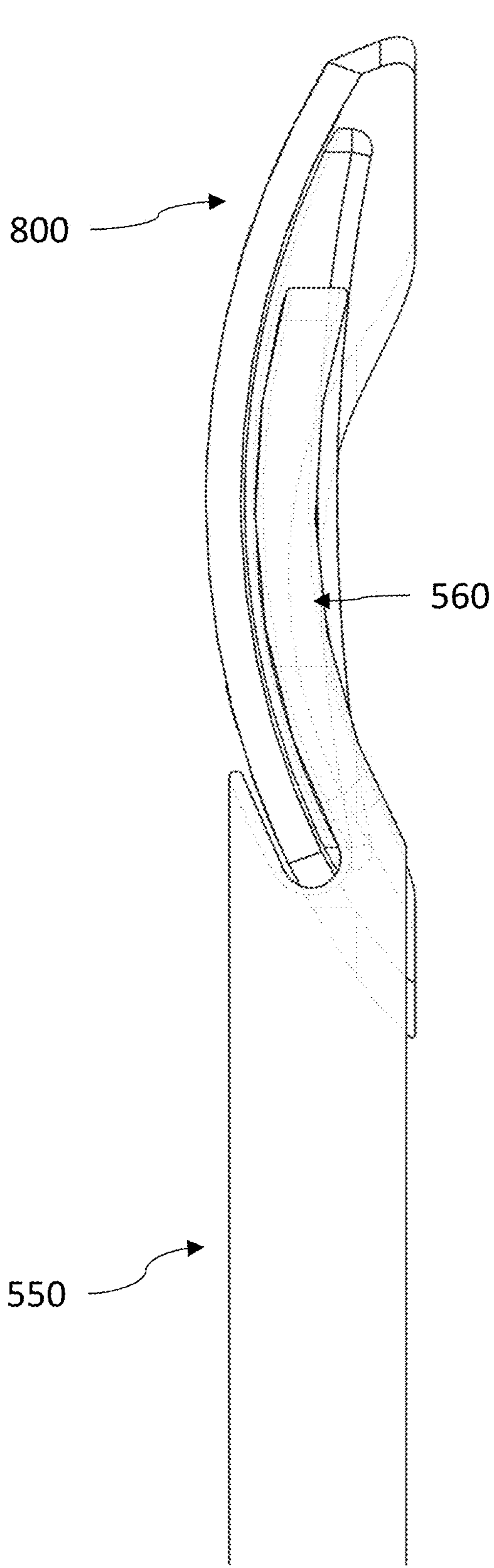
FIG. 13D is a non-limiting side view of the delivery stem and the spacer device of FIG. 13B, in accordance with non-limiting embodiments of the present disclosure.

FIG. 13D depicts a side view of the assembled components, further illustrating how the delivery rod 550 and engaging element 560 interface with the spacer device 800. In this view, the curvature of the spacer device 800 and the engaging element 560 is apparent, suggesting a conformal interface that may follow the natural contours of ocular anatomy. This ergonomic curvature may improve maneuverability and allow the device to rest against anatomical landmarks to aid in accurate positioning. The engaging element 560 is shown residing within a recessed portion of the spacer body, which may serve both to guide the delivery rod 550 during insertion and to protect the interface from lateral forces.

In alternate embodiments, the engaging element 560 may include features such as detents, resilient arms, or magnetic components to facilitate engagement. Likewise, the spacer device may include engagement receptacles or guide tracks shaped to receive and align the rod and its retention element with minimal play.

Materials may include biocompatible plastics, shape-memory alloys, or elastomeric polymers depending on the desired flexibility, reusability, or single-use nature of the device.

Practical Implementation

Described herein is a spacer device configured for placement in an eye, such as a human eye or animal eye. The spacer device can have a predetermined size, volume, diameter, length, cross-sectional shape, and/or geometry tailored for subconjunctival, subtenonique or suprachoroidal implantation to effect spacing, support, or modulation of tissue or fluid dynamics.

The spacer device can be delivered and positioned in the eye using a dedicated delivery device. In one embodiment, the delivery device comprises an elongated delivery member or cannula, which defines an internal lumen configured to house the spacer device. The distal end of the delivery member may include a sharpened or beveled cutting or piercing tip, adapted to penetrate the ocular surface or a selected tissue layer. The delivery member may further include a longitudinally movable delivery rod or plunger configured to eject the spacer device from the distal end.

Advantageously, the implantation procedure may be performed in a minimally invasive manner under topical anesthesia, obviating the need for general anesthesia or an operating room. In particular, the method may employ an ab externo approach (i.e., entering the eye from outside) thus minimizing trauma and reducing procedural complexity. The small profile of the delivery member and the self-expanding nature of the spacer device further contribute to procedural efficiency and safety.

A practical non-limiting implementation of such method will now be described with reference to method 1100 illustrated in FIG. 17.

At step 1110, the method includes positioning the distal end of the delivery member at a first target point on the ocular surface of the eye, such as the superior temporal quadrant of the conjunctiva. The positioning may be guided visually or optionally assisted by imaging or anatomical landmarks.

At step 1120, the method further includes advancing the delivery member along the longitudinal axis thereof until the distal tip contacts the target tissue surface, e.g., the conjunctiva or Tenon's capsule. Continued advancement of the delivery member causes the distal tip to incise the tissue, step 1120. The delivery member is inserted to a predetermined depth, positioning the distal tip at or near the desired implantation site. For example, the implantation site can be a subconjunctival, sub-Tenon's or suprachoroidal implantation site. The spacer device remains retained within the delivery member lumen during such insertion.

At step 1130, the method includes deploying the spacer device at the implantation site by actuating a control point. For example, the control point can be a manually operated, $CO_2$-actuated, or screw-driven actuator. The control point can actuate and control a delivery mechanism to drive the spacer device through the lumen of the delivery member and eject the spacer device out the distal tip.

In a specific implementation, during the travel of the spacer device through the lumen, the spacer device can reversibly transitions from an expanded configuration to a compressed configuration. For example, the spacer device can be stored within a lumen of the delivery member in the expanded configuration, and then transition to the compressed configuration when the delivery mechanism drives the spacer device into a distal tappered portion of the delivery member—the internal walls of the delivery member causing the spacer device to fold, e.g., along a longitudinal axis thereof.

During travel through the lumen of the delivery member, the spacer device is generally in a compressed configuration. Once the spacer device exits the distal tip of the delivery member, the spacer device expands into the expanded configuration. In some embodiments, the expansion may be driven by elastic memory, hydration, or other material properties. The spacer device may then serve as a mechanical spacer, support element, or drug-eluting structure, depending on design.

The spacer device can be used in conjunction with a channel in the eye that allows fluid to flow out of the eye internal chamber to reduce internal ocular pressure. In one embodiment, the spacer device is implanted adjacent to or in fluid communication with a surgical ostomy, such as in glaucoma filtration surgery. For example, the channel can be generated with a channel-generating device such as the one described in U.S. patent application Ser. No. 19/087,331 and/or Ser. No. 19/048,877, each of which is hereby incorporated by reference in their entirety.

For example, the spacer device can be used in conjunction with a glaucoma shunt implanted in the eye and that allows fluid to flow out of the eye internal chamber to reduce internal ocular pressure. For example, the glaucoma shunt can be any suitable shunt such as the one described in U.S. patent application Ser. No. 19/072,936 and/or PCT Patent application serial number PCT/CA2023/051644, each of which is hereby incorporated by reference in its entirety. The spacer device is implanted adjacent to or in fluid communication with a distal opening of the glaucoma shunt to receive fluid outflowing from the shunt into its cavity, such as in glaucoma subconjunctival implant placement. Alternatively, the spacer device can be placed such that at least a portion of its body is over the distal opening of the glaucoma shunt to receive fluid outflowing from the shunt into its cavity.

Unless otherwise defined, all technical and scientific terms used herein have the same meaning as commonly understood by a person of ordinary skill in the art to which the present invention pertains. As used herein, and unless stated otherwise or required otherwise by context, each of the following terms shall have the definition set forth below.

Other examples of implementations will become apparent to the reader in view of the teachings of the present description and as such, will not be further described here.

All references cited throughout the specification are hereby incorporated by reference in their entirety for all purposes.

Note that titles or subtitles may be used throughout the present disclosure for convenience of a reader, but in no way these should limit the scope of the invention. Moreover, certain theories may be proposed and disclosed herein; however, in no way they, whether they are right or wrong, should limit the scope of the invention so long as the invention is practiced according to the present disclosure without regard for any particular theory or scheme of action.

As used herein, the wording "independently selected" in reference to a group of specified items refers to the fact that when more than one item is selected from the group of items, the decision of selecting a specific item is not influenced by the decision of selecting any of the previous or following item(s).

Reference throughout the specification to "some embodiments", and so forth, means that a particular element (e.g., feature, structure, and/or characteristic) described in connection with the invention is included in at least one embodiment described herein, and may or may not be present in other embodiments. In addition, it is to be understood that the described inventive features may be combined in any suitable manner in the various embodiments.

It will be understood by those of skill in the art that throughout the present specification, the term "a" used before a term encompasses embodiments containing one or more to what the term refers. It will also be understood by those of skill in the art that throughout the present specification, the term "comprising", which is synonymous with "including," "containing," or "characterized by," is inclusive or open-ended and does not exclude additional, un-recited elements or method steps.

Unless otherwise defined, all technical and scientific terms used herein have the same meaning as commonly understood by one of ordinary skill in the art to which this invention pertains. In the case of conflict, the present document, including definitions will control.

As used in the present disclosure, when the terms "around", "about" or "approximately" are before a quantitative value, the present disclosure also includes the specific quantitative value itself, unless specifically stated otherwise. As used herein, the terms "around", "about" or "approximately" refer to a ±10% variation from the nominal value unless otherwise indicated or inferred.

Unless otherwise noted, the expression "at least" or "at least one of" as used herein includes individually each of the recited objects after the expression and the various combinations of two or more of the recited objects unless otherwise understood from the context and use. The expression "and/or" in connection with three or more recited objects should be understood to have the same meaning unless otherwise understood from the context.

The use of the term "include," "includes," "including," "have," "has," "having," "contain," "contains," or "containing," including grammatical equivalents thereof, should be understood generally as open-ended and non-limiting, for example, not excluding additional unrecited elements or steps, unless otherwise specifically stated or understood from the context.

Unless otherwise noted, the order of steps or order for performing certain actions is immaterial so long as the present invention remain operable. Moreover, two or more steps or actions may be conducted simultaneously.

Unless otherwise noted, the use of any and all examples, or exemplary language herein, for example, "such as" or "including," is intended merely to illustrate better the present invention and does not pose a limitation on the scope of the invention. No language in the specification should be construed as indicating any non-claimed element as essential to the practice of the present invention.

Furthermore, although the various embodiments and description may specify certain anatomical locations, species, or surgical procedures, it should be appreciated that these embodiments apply to other locations, species, and surgical procedures.

Although various embodiments of the disclosure have been described and illustrated, it will be apparent to those skilled in the art considering the present description that numerous modifications and variations can be made. The scope of the invention is defined more particularly in the appended claims.

We claim:

1. A spacer device for implantation in an eye, comprising a flexible body configured to conform to an anatomical tissue surfaces of the eye, wherein the body includes an internal surface and an external surface, wherein the spacer device is configured to reversibly transition between a compressed configuration suitable for delivery through a delivery member and an expanded configuration defining a convex, internal three-dimensional volume for receiving fluid from an anterior chamber of the eye, wherein the spacer device includes at least a pair of engaging elements centrally positioned on the internal surface and extending along a longitudinal axis of the spacer device, the engaging elements projecting perpendicularly from the internal surface and defining a central slot therebetween, and wherein the engaging elements are configured to (i) interface with the delivery member to stabilize the spacer device during implantation in the eye, (ii) engage with the tissue surface, and (iii) define, together with the central slot, an outflow path along the eye tissue surface engaged by the engaging elements to allow fluid to circulate therethrough.

2. The spacer device of claim 1, wherein the flexible body comprises a shape-memory biocompatible material.

3. The spacer device of claim 1, wherein the flexible body is configured to be compressed or folded along its longitudinal axis to facilitate insertion through the delivery member.

4. The spacer device of claim 1, wherein the engaging elements are further configured to engage with a corresponding delivery rod within the delivery member through at least a portion of the central slot.

5. The spacer device of claim 1, wherein the body has an undulating perimeter to facilitate fluid flow along lateral or posterior directions.

6. The spacer device of claim 1, wherein an anterior-facing portion of the body includes a relief cut-out configured to avoid contact with the cornea and to support anterior bleb formation.

7. The spacer device of claim 1, wherein a posterior portion of the body includes one or more cut-outs or elevated sidewalls configured to enable fluid migration and posterior bleb expansion.

8. The spacer device of claim 1, wherein the internal three-dimensional volume defined by the expanded configuration has a height at its apex of from about 600 μm to about 900 μm.

9. The spacer device of claim 1, wherein the device has a thickness of from about 0.4 mm to about 1.0 mm.

10. The spacer device of claim 1, wherein the device has a first diameter and a second diameter each independently ranging from about 2.5 mm to about 4.0 mm.

11. The spacer device of claim 1, wherein the engaging elements are integrally molded with the body and contribute to maintaining orientation of the spacer device during deployment.

12. The spacer device of claim 1, wherein the engaging elements are configured to anchor the device to the eye tissue surface, and wherein the eye tissue surface is the sclera or Tenon's capsule.

13. The spacer device of claim 1, wherein the spacer device is configured for subconjunctival, sub-Tenon's or suprachoroidal space implantation.

14. The spacer device of claim 1, wherein the body is oriented in situ with a curved surface facing the limbus and one or more legs extending posteriorly to direct aqueous humor flow.

15. The spacer device of claim 1, wherein the compressed configuration allows passage through the delivery member wherein the delivery member has a lumen having an internal diameter of less than 1 mm.

* * * * *